United States Patent [19]

Eggers et al.

[11] Patent Number: 5,766,167
[45] Date of Patent: Jun. 16, 1998

[54] MONOPOLAR ELECTROSURGICAL INSTRUMENTS

[75] Inventors: Philip E. Eggers, Dublin; Dennis Joseph Denen, Columbus, both of Ohio

[73] Assignee: United States Surgical Corporation, Norwalk, Conn.

[21] Appl. No.: 410,630

[22] Filed: Mar. 24, 1995

Related U.S. Application Data

[63] Continuation of Ser. No. 170,093, Dec. 17, 1993, abandoned.
[51] Int. Cl.$^6$ .................................................. A61B 17/39
[52] U.S. Cl. ........................... 606/46; 606/42; 606/52
[58] Field of Search ........................... 606/32, 34, 37, 606/42, 45, 52, 27, 31

[56] References Cited

U.S. PATENT DOCUMENTS

| | | |
|---|---|---|
| 3,946,738 | 3/1976 | Newton et al. . |
| 4,128,099 | 12/1978 | Bauer . |
| 4,994,024 | 2/1991 | Falk . |
| 5,100,402 | 3/1992 | Fan . |
| 5,122,137 | 6/1992 | Lennox ............................. 606/49 |
| 5,156,633 | 10/1992 | Smith . |
| 5,267,998 | 12/1993 | Hagen ............................... 606/46 |
| 5,269,780 | 12/1993 | Doos ................................. 60/651 |
| 5,312,401 | 5/1994 | Newton et al. . |

FOREIGN PATENT DOCUMENTS

| | | |
|---|---|---|
| 0041719 | 12/1981 | European Pat. Off. . |
| 0508453 | 10/1992 | European Pat. Off. . |
| 0530400 | 3/1993 | European Pat. Off. . |
| 0536440 | 4/1993 | European Pat. Off. . |
| 0547772 | 6/1993 | European Pat. Off. . |
| 93/00862 | 1/1993 | WIPO . |
| 9300862 | 1/1993 | WIPO . |

OTHER PUBLICATIONS

Tucker et al, "Capacitive Coupled . . . " Biomedical Instru. & Technology; 1992; 26:303–311.
"Electromagnetics" by Kraus, McGraw-Hill, Inc., Fourth Ed., pp. 73–88 and 161–166.
"Electrosurgery" by Pearce, John Wiley & Sons, pp. 247–248.
"Electrical Engineering Circuits" by Skilling, John Wiley & Sons, 1957, pp. 42–47.
Gyn. Laparoscopy–Double Puncture (10 mm) brochure by Olympus.
"Gym. Laparoscopy–Double Puncture (5 mm)–trocar tubes for instruments" by Olympus.
"Gyn. Laparoscopy–Double Puncture (5 mm) trocar tubes for 5 mm second puncture" by Olympus.
"Essentials of Monopolar Electrosurgery for Laparoscopy" by Voyles, et al., 1992 ElectroSurgical concepts, pp. 1–32.
"The Effect of Guidewires During Electrosurgical Sphincterotomy" by Johlin, et al., Gastrointestinal endoscopy, vol. 35, No. 5, 1992, pp. 536–540.

(List continued on next page.)

*Primary Examiner*—Michael Peffley

[57] ABSTRACT

A monopolar electrosurgical instrument for utilization with endoscopic and laparoscopic surgical procedures. The instrument is structured so as to substantially eliminate the adverse effects occasioned by capacitive coupling between the instrument and tissue adjacent thereto within the body being operated upon. Capacitive coupling is controlled through the implementation of the shaft structure itself with an electrically insulative polymeric material of low dielectric constant which is combined with a current conductor centrally disposed therein which is of minimum diameter effective to carry requisite current to a working tip. A shield arrangement may be provided such as a coextruded electrically conductive wire mesh surmounting the internally disposed electrical conductor. This shield, in one embodiment may be coupled with return ground employing electrical connectors which assure proper coupling with source and ground.

32 Claims, 13 Drawing Sheets

OTHER PUBLICATIONS

"Education and Engineering Solutions for Potential Problems with Laparoscopic Monopolar Electrosurger" by Boyles et al. American Journal of Surgery, vol. 164, 1992, pp. 57–62.

"Do Surgical Gloves Protect Staff During electrosurgical Procedures" by Tucker, et al. Surgery 1991 110:892–5.

"Radiofrequency Leakage Current from Unipolar Laparoscopic ElectroCoaggulators" by DiNovo, the Journal of Reproductive Medicine, vol. 28, No. 9, 1983, pp. 565–575.

"Capacitive Coupled Stray Currents During Laparoscopic and Endoscopic electrosurgical Procedures" by Tucker, et al. Biomedical Instrumentation and Technology; 1992; 26:303–311.

"Complication of Laparoscopic Tubal Sterilization" by Cunanan, Jr., et al., Obstetrics and Gynecology, 1989; 55–501–506.

"Electrical Hazards in Endoscopic Services" by Gullini, et al. Endoscopy, 1986; 211–212.

"Principals and Hazards in electrosugery Including Laparoscopy" by Neufeld, Surgery, Gynecoloyg & Obstetrics, 1978; 147:705–710.

"Electrosurgery in Laparoscopy" by Harris, The Journal of Reproductive Medicine; 1978; 21–48–52.

"The Laparoscopist and Electrosurgery" by Esposito Am. J. Obstet. Gynecol; 1976: 126:633–637.

"Complications of Flexible Fiber Optic Colonoscopy and Poly–Pectomy" by Rogers, et al. Gastrointestinal Endoscopy 1975; 22:73–77.

"The Electrical Dynamics of Laparoscopic Sterilization" by Engel, et al., The Journal of Reproductive Medicine, 1975 15:33–42.

"Electrosurgical Hazards in Laparoscopy" JAMA, 1974; 227:1261.

"Hazards in electroscopy Via the Fiber Optic Endoscope" by Hanwell, british Society for Digestive Endoscopy; 1973 vol. 14: 920.

"High Frequency Currents in Endoscopy: A Review of Principles and Precautions" by Curtiss, Gastrointestinal Endoscopy; 1973; vol. 14:920.

"A Method for Preventing Abdominal Burns Caused by Electrocautery During Laparoscopy" by Esposito, Am. J. Bostet. Gynecol.; 1972; 114:1105–1106.

"Electrosurgery Burns and the Urologist" by Goodman, The Journal of Urology; 1976; 116:218 220.

Electrical Safety Problems in Endoscopic Equipment by Drabkin, et al. Plenum Publishing 1988; 0006–3398/87/2104–0134–0138 translated from Meditsinskaya Tekhnika, No. 4, pp. 16–21, Jul.–Aug. 1987.

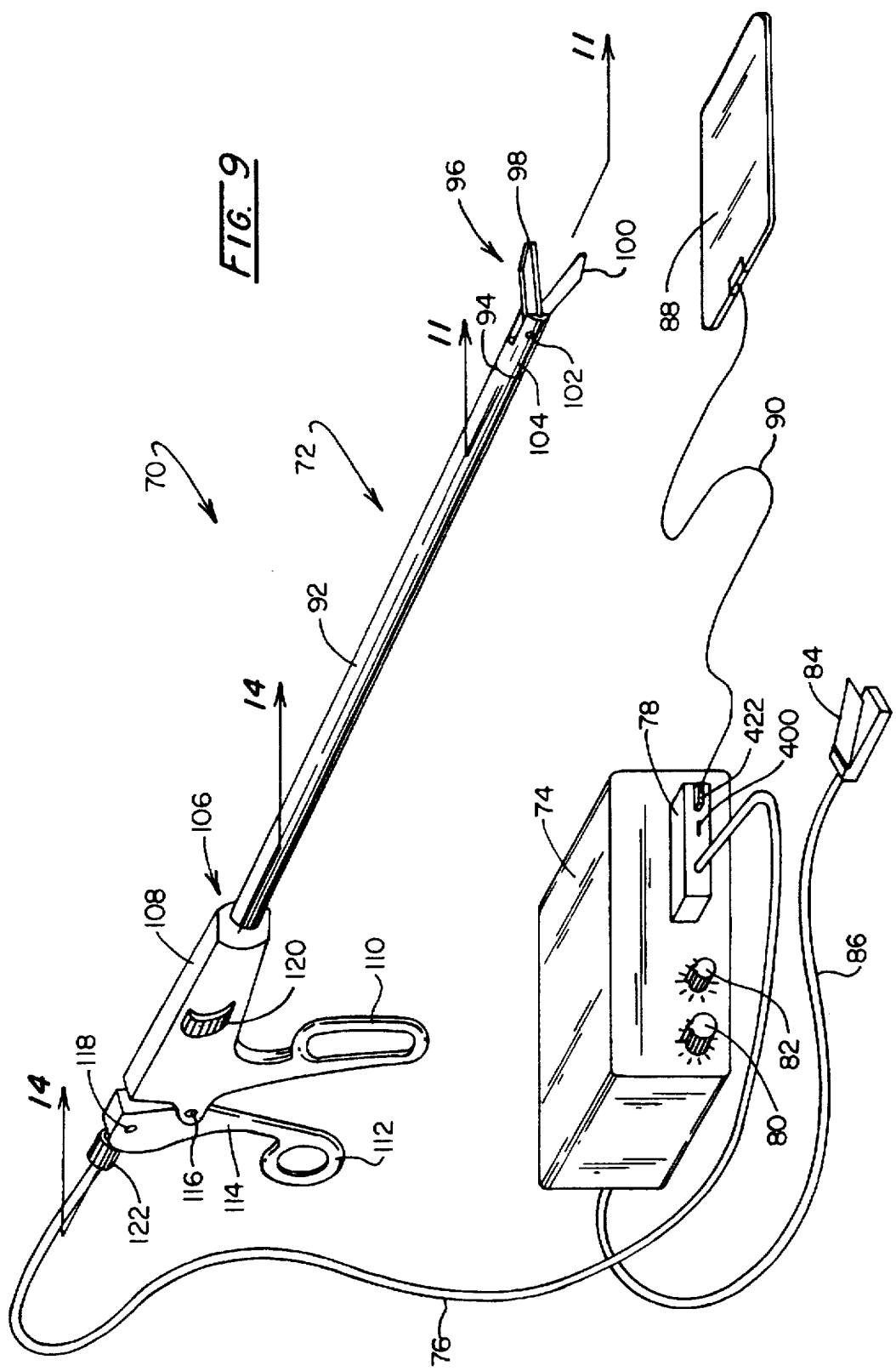

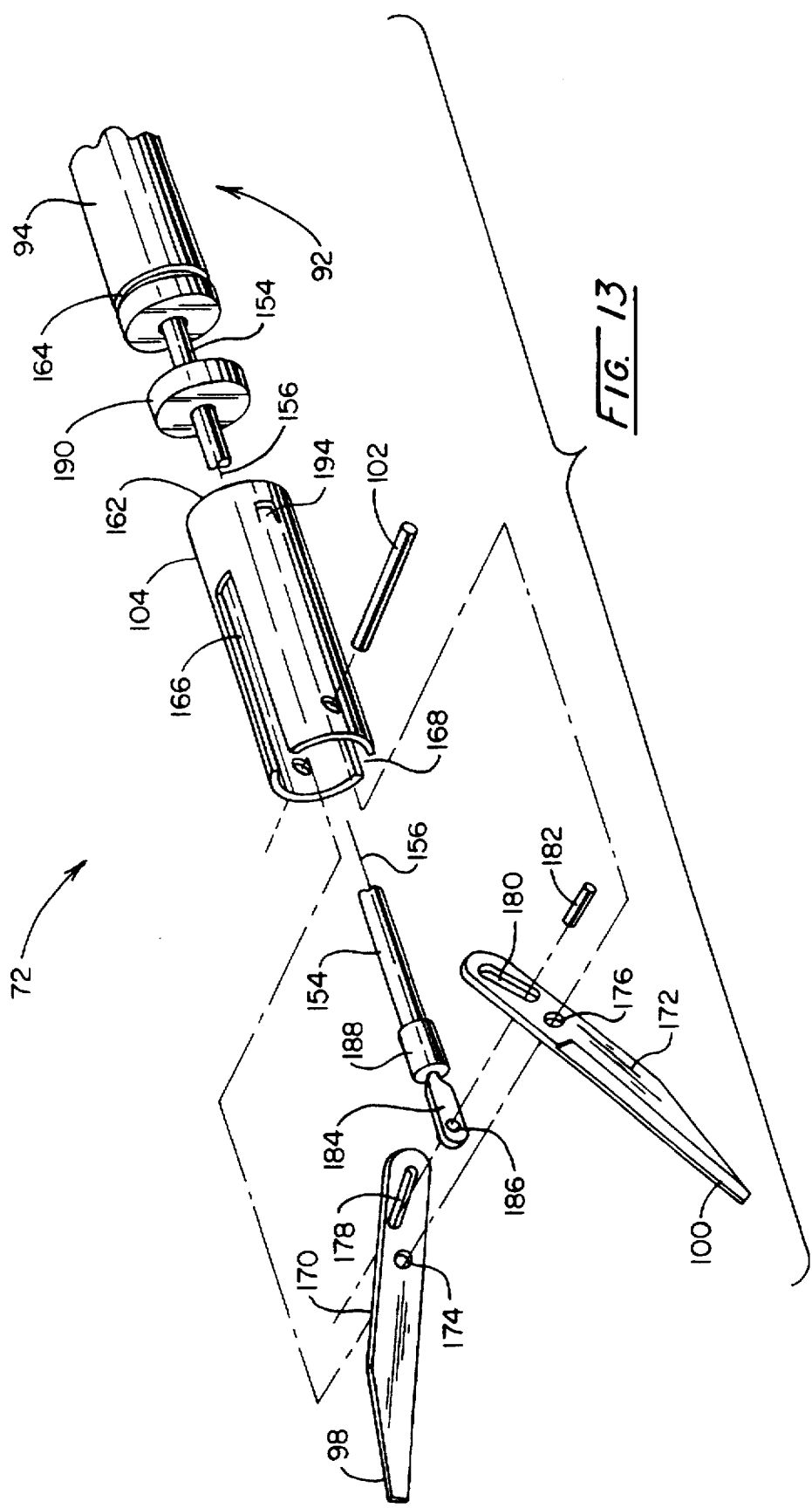

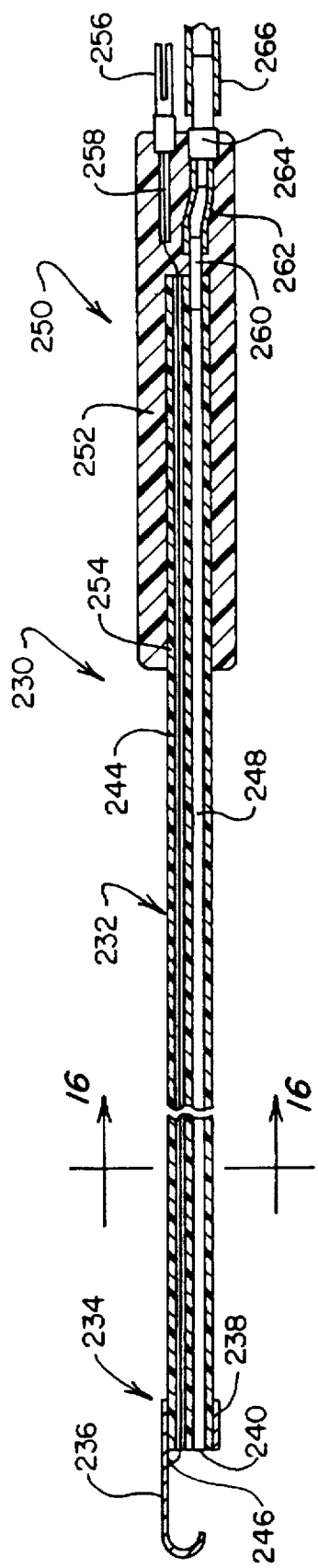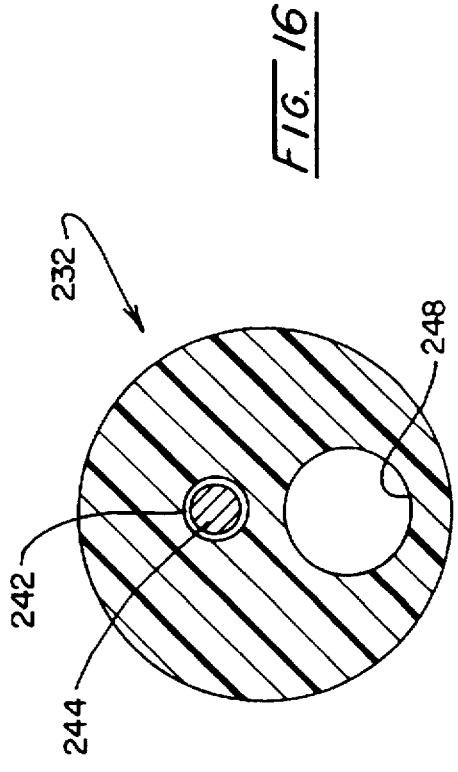

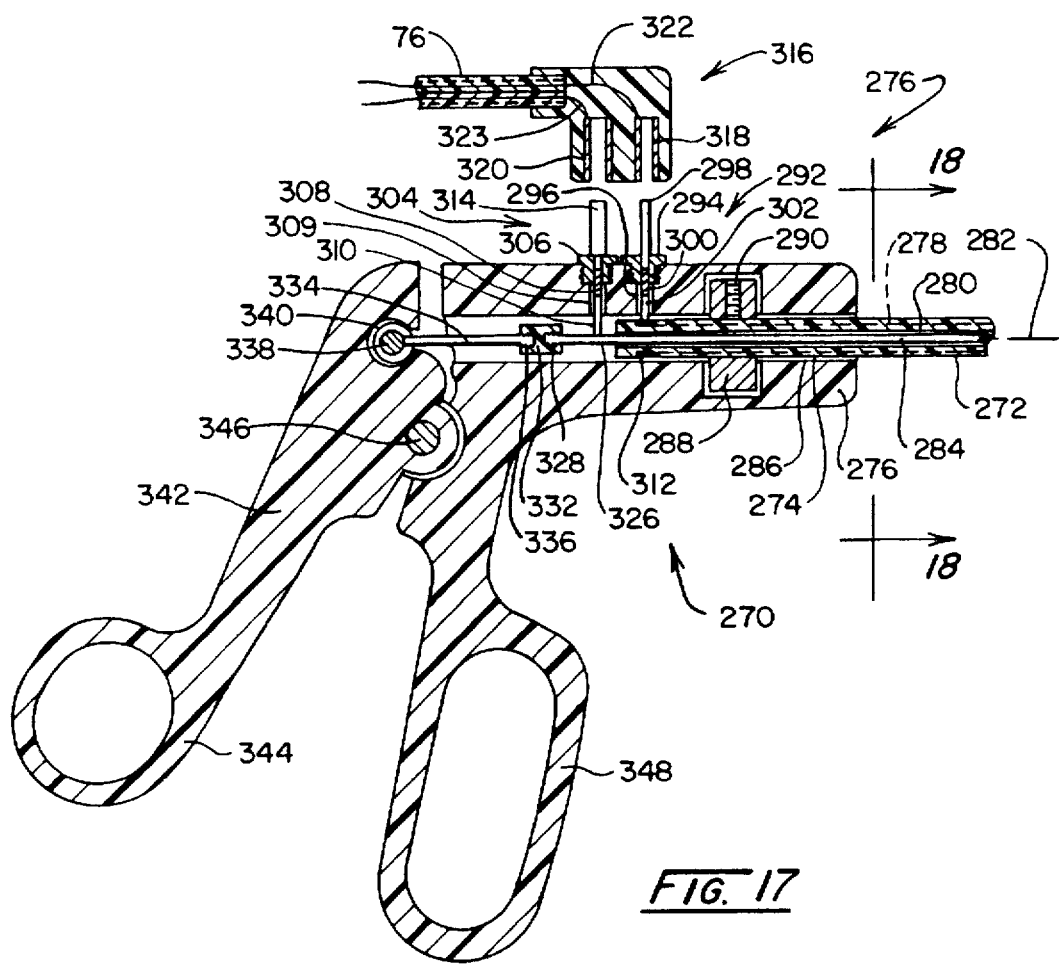
FIG. 17
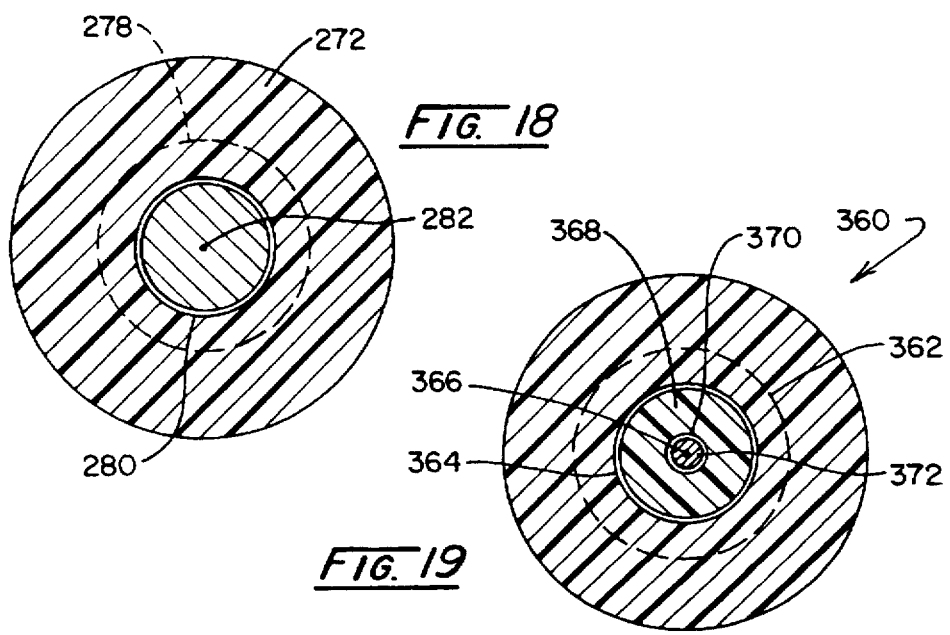
FIG. 18
FIG. 19

5,766,167

MONOPOLAR ELECTROSURGICAL INSTRUMENTS

This is a continuation of application Ser. No. 08/170,093, filed on Dec. 17, 1993 now abandoned.

BACKGROUND OF THE INVENTION

In "open" surgical procedures, the surgeon gains access to work inside the body by cutting large incisions through the body wall, then stretching the overlying tissue apart to provide visibility and room to manipulate his hands and instruments. Vital structures are generally held away from the surgical site and shielded from instruments by being covered with cloth pads. The surgeon can touch and manipulate the tissues. As the surgeon manipulates, cuts and dissects tissues, control is provided over the resultant bleeding by blotting or suctioning away the accumulating blood, enabling him to see the bleeding vessels and clamp and tie them off.

The creation of a large opening in the patient's body tissue greatly increases the risk of surgery to the patient's health, by increasing the probability of complications. Those complications can arise not only from treatment of the target tissue, i.e., that tissue necessitating the surgery, but also from the trauma caused to adjacent tissue in creating an opening providing the surgeon with access to the target tissue. Once the internal tissue is operated upon, the surgeon faces the time-consuming task of closing up the surgical site. In addition, the patient may require extensive post-operative care and an extensive hospital stay. Development of the endoscope, a miniaturized television camera that is inserted through either a puncture wound in the body wall or a natural orifice of the body to provide a video image of the inside of the body cavity, has enabled surgeons to perform surgery using specially designed surgical instruments that are inserted through small puncture wounds or body orifices. Some previously known devices have been constructed that enable a surgeon to operate on internal tissue while viewing manipulation of the instrument though an endoscope. One such device is described in Falk, U.S. Pat. No. 4,994,024. Such previously known endoscopic instruments have several disadvantages, especially the inability to effectively stem blood from incised tissue.

Laparoscopic/endoscopic surgery avoids a large gaping incision through the body wall as called for in open surgery, and permits patients to undergo some major surgeries practically pain-free, with little or no post-operative hospital stay. However, in performing such surgery the surgeon foregoes manual access to the tissues being operated upon. In doing so, the traditional means of controlling bleeding by clamping and tying off transected blood vessels generally are not available. Consequently, in laparoscopic/endoscopic surgery it is important that bleeding is controlled or completely stopped in any tissues that are cut.

Hemostatic surgical techniques are known for reducing the bleeding from incised tissue during open surgical procedures, i.e., where overlying body tissue is severed and displaced to gain access to internal organs. Such techniques include electrosurgery, that is, passing a high frequency or radio frequency current (in the range from 100 to 5000 KHz) through a patient's tissue between two electrodes for cutting and coagulating the blood vessels contained within the tissue. The current passing through the tissue causes joulean (ohmic) heating of the tissue as a function of the current density and the resistance of the tissue through which the current passes. This heating dehydrates the tissues and denatures the tissue proteins to form a coagulum which seals bleeding sites, so that the body's own collagen is reformed on the cut surface, sealing the tissues against bleeding.

Endoscopic/laparoscopic electrosurgical techniques have been limited primarily to monopolar devices. Previously known monopolar electrosurgical instruments employ a small electrode at the end of a handle in the surgeon's hand and a large electrode plate beneath and in contact with the patient. Only one of the two electrodes required to complete the electrical circuit is manipulated by the surgeon and placed on or near the tissue being operated upon. The other electrode has a large area (typically 5 to 50 in$^2$) in contact with the exterior (skin) of the patient. A power supply impresses a high frequency voltage of thousands of volts between the two electrodes of the electrosurgical instrument, sufficient to cause arcing from the small opening electrode the surgeon holds to the most proximate tissues, then through the patient to the large return electrode in contact with the exterior surface of the patient. In the patient, the electrical current becomes converted to heat; hottest in the tissues immediately below the small hand-held electrode where the currents are most concentrated. Devices, such as the endoscopic monopolar coagulation forceps described in Bauer, U.S. Pat. No. 4,128,099; laparoscopic cauterization electrode described in Fan, U.S. Pat. No. 5,100,402; forceps Model No. A5261 and hook electrode Model No. A5268, available from Olympus Corporation Medical Instrument Division, Milpitas, Calif., are representative of such monopolar instruments.

While monopolar devices have proven useful in open surgical procedures, where the surgeon is able to view the effects of the current arc, the problems encountered in open surgical procedures become even more important in endoscopic surgical applications. In particular, when using a monopolar device endoscopically or laparoscopically, the surgeon's view of the electric arc generated by the instrument is restricted by the limited and greatly magnified field of view provided by the endoscope. Consequently, aberrant current arcs—the existence of which the surgeon may not even be aware—can cause deep tissue necrosis and inadvertent damage to adjacent tissue masses over the remaining length (30 cm or more) of the cannula or instrument shaft which is outside the field of view of the surgeon (i.e., outside the field of view of the endoscope which is focused only on the operative site).

The foregoing limitation has proven especially dangerous for surgeries performed in the abdomen, and in the vicinity of the peritonea and bowel wall. Practical experience has established that aberrant current arcs generated by endoscopic monopolar devices can cause perforation of the adjacent bowel wall when used on abdominal tissue masses. While such damage typically is not apparent to the surgeon during the procedure, it may later be manifested as peritonitis, which results in death in as many as 25% of all such cases.

One difficulty encountered with the use of conventional monopolar laparoscopic/endoscopic surgical instruments is caused by the capacitive coupling to surrounding tissue associated with high frequency voltage imposed on the electrically conductive member(s) within the shaft and handle of laparoscopic/endoscopic instruments. Construction of conventional monopolar endoscopic instruments permits such high voltages to be applied to electrically conductive members within and located close to the outer surface of the shaft. By way of example, a typical monopolar endoscopic instrument comprises a handle portion; a shaft having an outside diameter of 5 mm and a length of 33 cm;

a working end located at its distal end for purposes of cutting, grasping, coagulation or other treatment of tissue during a procedure. The shaft may include a driveshaft or rod for actuation of cutting or grasping components at working end. Also included is an electrically conducting, elongated tubular member or barrel which serves as both a support for the working end and an electrical connection between the high voltage source and the working end of the instrument. The electrically conducting, elongated barrel typically is constructed using stainless steel or aluminum-based alloys. The entire outer surface of the elongated metallic barrel (extending from the handle to the working end) is covered with 0.010 to 0.020 inch (0.50 to 0.63 mm) thickness of electrically insulating material (e.g., polyolefin shrink tubing) to prevent unwanted electrical contact with and associated heating of tissue that may touch the shaft proximal to the working end.

Although an intact, electrically insulating covering or sheath over the electrically conducting elongated barrel can prevent direct contact with tissue, it cannot prevent the transfer of energy to tissue by means of capacitive coupling. Capacitive coupling occurs in any situation where two electrically conductive members are in close proximity with one another even if separated by an electrically insulative member (e.g., polyolefin shrink tubing or any other electrically insulating material). The higher the relative dielectric constant (also known as relative permitivity), the larger the magnitude of capacitive coupling which, in turn, leads to correspondingly higher current flow between the elongated barrel and tissue. By the mechanism of capacitive coupling, tissue which may come in contact with the surface of the shaft may be heated by current flow which can result in unwanted and unobserved thermal damage to tissue (e.g. bowel) which can lead to subsequent perforation and peritonitis.

Yet another difficulty encountered with the use of conventional monopolar endoscopic surgical instruments is the failure of the electrical insulation (e.g., heat shrink tubing) which surrounds the electrically active metal tube barrel (25 to 45 cm in length) which extends from the proximal end (e.g., handle) to the distal operative end (e.g., scissors, forceps or hook electrode). Electrically insulated coverings may become damaged, exposing the electrically active metal barrel, as a result of mechanical cutting or abrasion with repeated insertion and removal from the surgical introduction port or through contact with other sharp or abrasive instruments during normal use, cleaning and sterilization. The presence of even a very small defect (e.g., too small to be observable with the unaided eye) in the integrity of the electrically insulative covering or coating can lead to unexpected and possibly unobserved arcing to any tissue that may come in contact with such defect.

Yet another difficulty encountered with the use of conventional monopolar endoscope instruments is the failure of the electrical insulation which covers the surface of the handle, the presence of even a very small defect (e.g., too small to be observable with the unaided eye) in the integrity of the electrically insulative covering or coating on the handle portion can lead to unexpected arcing and burn to the surgeon's hand. The result of such an unexpected burn may disrupt the surgeon's control and precision during the course of a surgical procedure.

For futher information concerning the subject at hand, the reader's attention is directed to the following publications:
1. "Essentials of Monopolar Electrosurgery for Laparoscopy" by Voyles and Tucker, 1992, *ElectroSurgical Concepts*, Laser Centers of America, Cincinnati, Ohio.
2. "The Effect of Guidewires During Electrosurgical Sphincterotomy", by Johlin, Tucker, and Ferguson, *Gastrointestinal Endoscopy*, Vol. 35, No. 5, 1992, pp. 536–540.
3. "Education and Engineering Solutions for Potential Problems with Laparoscopic Monopolar Electrosurgery" by Boyles and Tucker, *American Journal of Surgery*, Vol. 164, 1992, pp. 57–62.
4. "Radiofrequency Leakage Current from Unipolar Laparoscopic ElectroCoagulators" by DiNovo, *The Journal of Reproductive Medicine*, Vol. 28, No. 9, 1983, pp. 565–575.
5. "Capacitive Coupled Stray Currents During Laparoscopic and Endoscopic Elecctrosurgical Procedures" by Tucker, Voyles, and Silvis, *Biomedical Instrumentation & Technology*; 1992; 26:303–311.
6. "Complications of Laparoscopic Tubal Sterilization" by Cunanan, Jr., Courey, and Lippes, *Obstetrics & Gynecology*; 1980; 55:501–506.
7. "Electrical Hazards in Endoscopic Services" by Gullini, Caselli, and Cantarini, *Endoscopy*; 1986; 211–212.
8. "Principals and Hazards of Electrosurgery Including Laparoscopy" by Neufeld, *Surgery, Gynecology & Obstetrics*; 1978; 147:705–710.
9. "Electrosurgery in Laparoscopy" by Harris, *The Journal of Reproductive Medicine*; 1978; 21:48–52.
10. "The Laparoscopist and Electrosurgery" by Esposito, *Am. J. Obstet. Gynecol.*; 1976; 126:633–637.
11. "Complications of Flexible Fiber Optic Colonoscopy and Polypectomy" by Rogers, et al., *Gastrointestinal Endoscopy*; 1975; 22:73–77.
12. "The Electrical Dynamics of Laparoscopic Sterilization" by Engel and Harris, *The Journal of Reproductive Medicine*; 1975; 15:33–42.
13. "Electrosurgical Hazards in Laparoscopy", JAMA 1974; 227:1261.
14. "Hazards in Electrosurgery Via the Fiber Optic Endoscope" by Hanwell, British Society for Digestive Endoscopy; 1973; Vol. 14: 920.
15. "High Frequency Currents in Endoscopy: A Review of Principles and Percautions" by Curtiss, *Gastrointestinal Endoscopy*; 1973; 20:9–12.
16. "A Method for Preventing Abdominal Burns Caused by Electrocautery During Laparoscopy" by Esposito, *Am. J. Obstet. Gynecol.*; 1972; 114:1105–1106.
17. "Electrosurgery Burns and the Urologist" by Goodman, *The Journal of Urology*; 1976; 116:218–220.
18. "Electrical Safety Problems in Endoscopic Equipment" by Drabkin, et al., Plenum Publishing Corporation, 1988; 0006–3398/87/2104–0134–0138, translated from *Meditsinskaya Tekhnika*, No. 4, pp. 16–21, July-Aug. 1987.
19. "Do Surgical Gloves Protect Staff During Electrosurgical Procedures?", by Tucker, et al.,*Surgery*, 1991; 110:892–5.

A method has been described by Newton (International Application No. PCT/US92/05576, International Publication No. WO03/00862) to minimize the hazards to the patient as a result of both capacitive coupling and failure of (i.e., defect in) the outer electrically insulating covering in the region of the elongated electrically conducting barrel. This method employs an outer tubular sheath which surrounds part or all of the exposed length of the shaft proximal to the working end of the instrument. Such sheath comprises an electrically conducting shielding member which is connected to an electronic sensing and switching arrangement connected to the high voltage energizing source. The electronic sensing and switching allows electromagnetic energy to be shielded from tissue under normal conditions and interrupts the application of high voltage to the endoscopic instrument under abnormal conditions (e.g., significant failure of insulative covering over the metallic elongated barrel of endoscopic instrument or interruption of connection between shielding member and return electrode).

It would be desirable to provide monopolar electrosurgical instruments for hemostatically severing or treating tissue in laparoscopic/endoscopic surgical procedures which remains straightforward in structure while overcoming the disadvantages of previously known instruments with a high level of assurance. Such instruments would enable a large number of operations to be carried out safely using laparoscopic/endoscopic techniques, thereby reducing the risks to the patient and surgeon associated with existing monopolar electrosurgical instruments.

SUMMARY

The present invention is addressed to monopolar electrosurgical instruments and their use in endoscopic/laparoscopic procedures. These instruments are structured to substantially minimize or, in effect, eliminate opportunities for tissue damage occasioned by aberrant current arcs developed upon the occasion of capacitive coupling phenomena. Thin insulative coverings provided with instruments of the past are eliminated and recognition is made that the outer insulative surface of the instrument at the interface thereof with body tissue represents a capacitor half element. By substantially reducing the effective size of the complementing half element while correspondingly increasing the low dielectric constant parameter between these two half elements, leakage currents associated with capacitive coupling are reduced to a minimum. To implement this approach, the instrumentation preferably employs a current carrying conductor at the center of the instrument which is the minimum principal dimension, i.e. diameter as compared with the overall diameter of the instrument shaft itself. The shaft is formed of an electrically insulative, low dielectric constant material and the ratio of the diametric dimensions of the conductor and the outer surface of the shaft becomes quite high to essentially eliminate the occasion for capacitive coupling.

Where the working end of the instrument supports some form of a reciprocally actuated working tip such as a scissors or grasper, then the advantage of the inventive structuring can be maintained through the utilization of an electrically insulative, low dielectric constant polymeric material as the driveshaft formed internally within the instrument outer shaft. This drive shaft then may function as the support for the otherwise weak and thin electrical conductor extending from the handle of the instrument to its working tip.

As another aspect of the invention, the electrically insulative polymeric shaft of the instrument is employed with an electrically conductive shield surrounding the internally disposed conductor carrying current to the working tip. Where that internal conductor is of minimum effective diameter, then stray current phenomena are controlled both by the guarding shield and by the minimization of the size of the capacitor half element represented by the current carrying component wherein the shield is coupled to the patient return ground. However, for this implementation, it is of value to assure proper connection always is made through the utilization of mutually incompatible terminal structures for applied current and return ground.

As another aspect, the invention provides an instrument for carrying out monopolar electrosurgical procedures upon tissue within a body in contact with a return ground by insertion of the instrument through minimal size openings to access the tissue. The instrument includes an elongate shaft of length along a given axis suited for accessing the tissue, having a working end, a grasping end, and a surface at a first principal cross-sectional dimension such as a diameter permitting the slidable insertion of the instrument through the opening into the body. The shaft is formed of a polymeric, electrically insulative material. An electrically conductive working tip assembly is supported at the working end of the shaft which is responsive to an applied current at predetermined frequency for surgical application to select portions of the tissue. An electrical terminal is supported at the shaft grasping end having an input connectable with a source of the current and an output. An electrical conductor is supported within the shaft which extends therealong in current transfer communication between the electrical terminal and the working tip, and has a second principal cross-sectional dimension substantially less than the first principal cross-sectional dimension which is selective as effective to convey the applied current to the working tip and to lower capacitive coupling between the conductor and the tissue adjacent the shaft surface to an extent substantially atraumatic to adjacent tissue.

As another aspect, the invention provides a monopolar electrosurgical instrument for carrying out surgical procedures upon tissue within a body in contact with a return ground by insertion through access openings of minimal size. The instrument includes an elongate shaft of length along a central axis suited for accessing tissue having a working end, a grasping end, a surface at a first principal cross-sectional dimension permitting a slidable insertion thereof through the opening into the body, the shaft being formed of a polymeric electrically insulative material and having a first elongate cavity disposed therein of second principal cross-sectional dimension. An electrically conductive working tip assembly is supported at the shaft working end which is reciprocally actuable to surgically engage the tissue and is responsive to an applied current at predetermined frequency for surgical application to select portions of the tissue. A hand-engageable handle is coupled with the shaft at the grasping end and has a movable component with a drive portion generally reciprocally movable in correspondence with the movement of the movable component. An elongate driveshaft formed of a polymeric, electrically insulating material, having an outwardly disposed surface extending about a longitudinal axis at a second principal cross-sectional dimension is slidably positioned within the first elongate cavity and extends between a forward end connected in reciprocal drive relationship with the working tip and a rearward portion connected in reciprocally driven relationship with the handle movable component drive portion. An electrical terminal is supported at the handle having an input connectable with a source of the current and an output, and an electrical conductor is supported within the driveshaft which extends therealong in current transfer communication between the electrical terminal and the electrically conductive working tip.

As a further aspect, the invention provides an instrument for carrying out monopolar electrosurgical procedures upon tissue within a body in contact with a return ground by insertion of the instrument though minimal size openings to access the tissue. An elongate shaft is provided of length along a central axis suited for accessing the tissue, having a working end, a grasping end, a surface at a first principal cross-sectional dimension permitting a slidable insertion thereof through the opening into the body. The shaft is formed of a polymeric electrically insulative material and has an elongate cavity disposed therein of second principal cross-sectional dimension. An electrically conductive working tip assembly is supported at the working end of the shaft which is reciprocally actuable to surgically engage the tissue and is responsive to an applied current at predetermined frequency for surgical application to selected portions of the tissue. A hand engageable handle is coupled with the shaft at the grasping end and has a movable component with a drive portion generally reciprocally movable in correspondence with movement of the movable component. An elongate driveshaft formed of electrically conductive material is provided having an outwardly disposed surface extending about a longitudinal axis at a second principal cross-sectional dimension. The driveshaft is slidably positioned within the elongate cavity and extends between a forward end connected in current transfer and reciprocal drive relationship with the working tip and a rearward portion connected in reciprocally driven relationship with the handle movable component drive portion. An electrically conductive shield is located within the shaft outwardly of the cavity and inwardly of the outwardly disposed surface in space surrounding relationship and substantially coextensive with the cavity. An electrical terminal assembly is supported at the handle which has a first input connectable with a source of the current, a second input connectable with the return ground, and has a first output connecting the drive shaft in current transfer relationship with the first input, and a second output connecting the second input with the shield.

Other objects of the invention will, in part, be obvious and will, in part, appear hereinafter. The invention, accordingly, comprises the apparatus and system possessing the construction, combination of elements, arrangement of parts which are exemplified in the following disclosure.

For a fuller understanding of the nature and objects of the invention, reference should be had to the following detailed description taken in connection with the accompanying drawings.

BRIEF DESCRIPTION OF THE DRAWINGS

FIG. 9 is a pictorial representation of an electrosurgical system according to the invention;

FIG. 13 is a partial exploded view of the instrument working end shown in FIG. 11;

FIG. 15 is a partial sectional view of a fixed tip electrosurgical instrument according to the invention;

FIG. 16 is a sectional view taken through the plane 16—16 shown in FIG. 15;

FIG. 17 is a partial sectional view of another embodiment of the invention;

FIG. 18 is a sectional view taken through the plane 18—18 shown in FIG. 17;

FIG. 19 is a sectional view of a shaft component of an instrument according to the invention showing an alternate shielded arrangement;

DETAILED DESCRIPTION OF THE INVENTION

Figure 1:
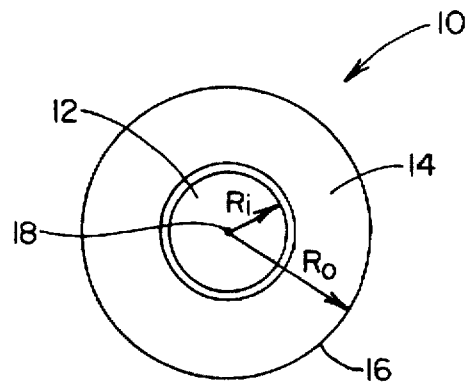
FIG. 1 is a schematic representation of a shaft component incorporating an internally disposed conductor employed in an analytical discussion of the system of the invention.

The endoscopic or laparoscopic electrosurgical instruments of the invention necessarily have a similarity in geometry of length and diameter as well as in functional implementation by the surgeon with devices currently in the marketplace. However, the design of these instruments, while constrained by those surgical requirements, varies in a manner achieving a very minimum opportunity for capacitive coupling between the instrument and adjacent tissue or other instrumentation such as cannulas, other instruments in the body cavity. Two general topologies are presented in the discourse to follow, a preferred one wherein current for electro-surgical purposes is conveyed by a very small internally disposed conductor to a working tip of the instrument and that internal conductor is surmounted by a shaft of electrically insulative material forming a dielectric, as it were, to the tissue through which is is moved. The second, less preferred embodiment involves the utilization of an internally disposed conductor but in conjunction with a circumferential (e.g. cylindrically shaped) shield which surmounts the internal conductor and which itself may be embedded within the electrically insulative material wherein such shield is coupled to instrument ground or patient return potential.

As a prelude to considering the design of the instrumentation, an analysis is provided as to capacitive coupling first in conjunction with the subject of coaxial conductors which, for analytical purposes, may be utilized as a model for analysis of the present instruments. Next, the analysis turns to non-coaxial capacitive systems, following which the instrumentation itself is described in detail.

The capacitance (in Farads) of coaxial conductors can be expressed as follows:

$$C = \frac{2\pi\epsilon\epsilon_o L}{\ln(R_o/R_i)} \quad \text{(Equation 1)}$$

where:

L=length of coaxial conductor $\epsilon$=relative dielectric constant of material between conductive members $\epsilon_o$=dielectric constant of free space $R_o$=radius of outer conductive member $R_i$=radius of inner conductive member For a given length of elongated barrel, L, and dielectric material (e.g. polysulfone) used in the construction of concentric electrically insulative tubes, the capacitance depends only on the relative radii of the two conductors as shown in the denominator of Equation 1. Expressing Equation 1 in terms of the capacitance factor, $F_c$, obtains:

$$C = (2\pi\epsilon\epsilon_o L) * F_c \quad \text{(Equation 2)}$$

where $$F_c = \frac{1}{\ln(R_o/R_i)} \quad \text{(Equation 3)}$$

See J. A. Pearce, *Electrosurgery*, pp 247–248, John Wiley & Sons, New York, 1986.

Maximum peak-to-peak current, Ipp, in a purely capacitive circuit can be estimated as follows:

$$Ipp = 2\pi f C Vpp \quad \text{(Equation 4)}$$

where $V_{pp}$=applied peak-to-peak voltage (Volts)

f=alternating current frequency (Hertz)

C=capacitance (farads)

As seen in Equation 4, for a given applied voltage level $V_{pp}$, the higher the capacitance, the higher the corresponding current that can flow in the circuit.

See H. H. Skilling *Electrical Engineering Circuits*, John Wiley & Sons, New York, 1961, pp. 42–46.

Referring to FIG. 1, a diagram is provided of a coaxial system represented generally at 10. System 10 shows in section an internally disposed electrical conductor 12 having an axis 18 and illustrating a representation, Ri, of the radius of the inner conductive member 12 as considered in the above equation. Similarly, the outer radius, Ro is represented as extending through electrically insulative, low dielectric value material ($\epsilon$) 14. The outer boundary for the demonstration as at 16 may be considered the tissue abutment interface or a shield.

Figure 2:
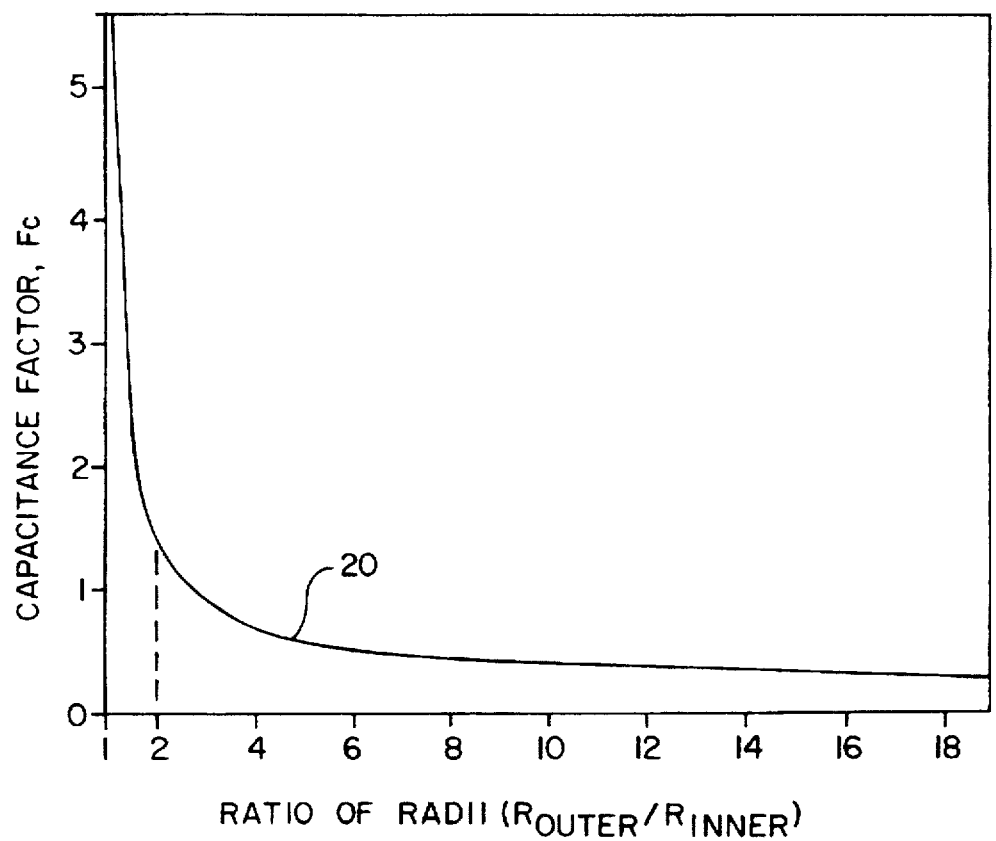
FIG. 2 is a graphical presentation of the relationship between capacitance and geometry of concentric electrically conductive members.

Looking to FIG. 2, a graph is presented at 20 illustrating the relationship between the ratio of the outer and inner conductors as compared with the capacitance factor, Fc, as discussed above in connection with Equation 3. The figure reveals that the capacitance factor, Fc, as well as the capacitance, C, become very large as the ratio of the radii of the conductors decreases below about 2. As a consequence of the inverse natural logarithm, the capacitance factor is reduced by a diminishing amount as the ratio of radii or diameter exceeds about 10. It may be observed that the greatest gains in reducing the capacitance, and therefore the hazards associated with capacitive coupling to tissue can be realized by increasing the ratio of radii or diameter to at least about 2.

Based on Equation 3 and the dimensions of the electrically conductive barrel and outer electrically insulative covering associated with conventional monopolar electrosurgical instruments, the capacitance factor, $F_c$, for endoscopic/laparoscopic instruments having a shaft diameter of 5 mm ranges from 4.5 to 9.5; the capacitance factor for endoscopic/laparoscopic instruments having a shaft diameter of 10 mm ranges from 9.5 to 19.5

Figure 3:
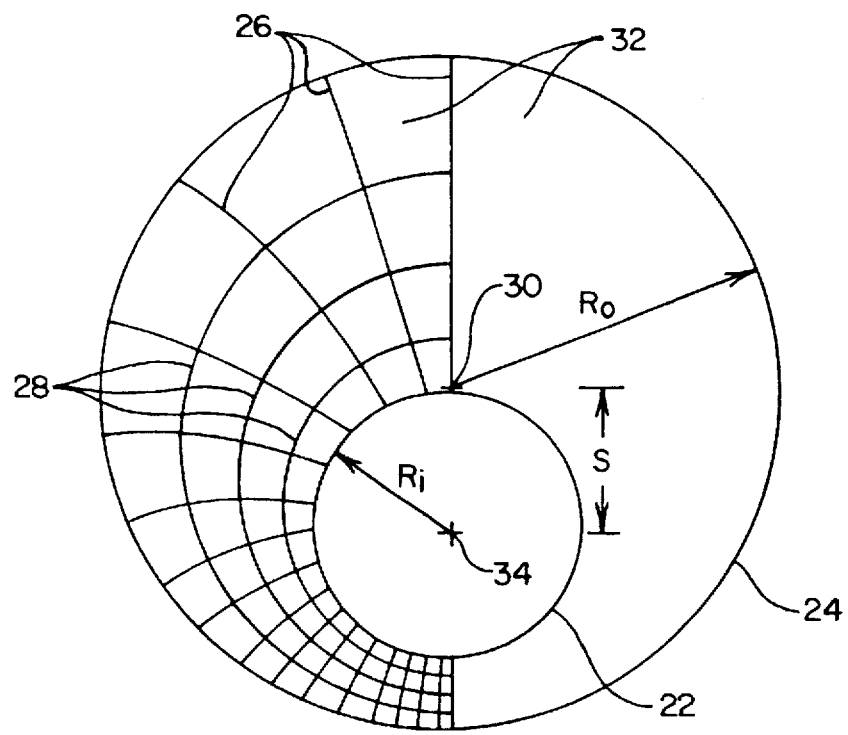
FIG. 3 is an illustrative representation of an instrument shaft according to the invention within an off axis internal conductor showing field mapping analysis.

The above relationship of capacitance and leakage current to relative radii of inner and outer electrically conductive members is for coaxial configurations wherein the inner and outer conductive members have the same axis as described at 18 in FIG. 1. Referring to FIG. 3, for the case of an arbitrary arrangement of an inner conductive member 22 and an outer conductive member which may be present as tissue, for example as located at 24, the capacitance can be estimated using the technique known as "field mapping" as described, for example, in the following publication:

Kraus, J. D., Electromagnetics, McGraw-Hill, Inc., New York, N.Y., 1988, pp 73–88, 161–166.

Figure 4:
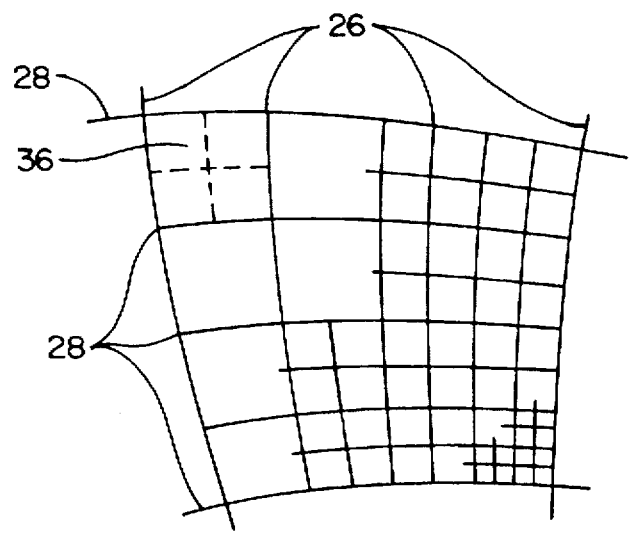
FIG. 4 is an enlarged fragment of the illustration of FIG. 3.

The field mapping technique is based on the principle of orthogonality between electric field lines 26 and equipotential surfaces 28, i.e., the field lines 26 and equipotential lines (or surfaces) 28 must intersect each other at right angles. Consequently, the field between two electrically-conductive members 22 and 24 can be sub-divided into geometrical shapes approximating squares which are often referred to as curvalinear squares. The curvalinear square is a four-sided area with electric field lines 26 and equipotentials 28 intersecting at right angles which tends to yield true squares as it is sub-divided into four parts, then each into four smaller parts. An isolated illustration of a curvalinear square is represented in FIG. 4.

Figure 5:
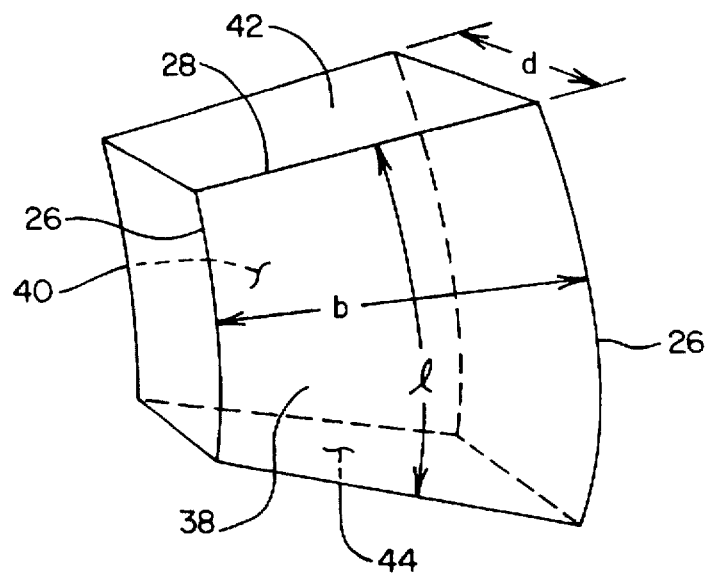
FIG. 5 is a three-dimensional illustration of a fragment of FIG. 4 with metal foils assumed to be applied to equipotential surfaces.

Returning to FIG. 3, assume that the inner conductive member 22 is a cylinder and is positioned off the center axis 30 of the outer cylindrical conductor 24, separation being by a dielectric material 32. The center axis of the inner conductive cylinder 22 is represented at 34. Due to the symmetry of conductors 22 and 24, only one-half of the space between the conductors needs to be mapped, since the other half is a mirror image. By appropriate selection of the interval between the field lines 26 and equipotential surfaces 28, the area enclosed between adjacent pairs of field lines and equipotential surfaces is a square or a curvalinear square (i.e., a "square" whose transverse mid-lines seen in FIG. 4 at 36 are equal). By this process, a field map is obtained wherein the region contained between two conductive surfaces is divided into many squares or curvalinear squares. Each such square represents a side of a field cell as illustrated in connection with FIG. 5. Looking to that figure, the three-dimensionally illustrated cell is seen to have a depth, d, between surfaces 38 and 40. The field cell has a transverse mid-line length, l (parallel to the electric field) seen extending between cell surfaces 42 and 44 which is equal to the orthogonal transverse mid-line width, b (parallel to the potential lines or surfaces).

If thin metal foils are applied to equipotential surfaces 42 and 44 of the illustrated field cell, there is obtained a field cell capacitor. The capacitance, C, of a parallel-plate capacitor (see Kraus, supra, at 162) is:

$$C = \frac{\epsilon \epsilon_o A}{1} \quad \text{(Equation 6)}$$

where $\epsilon$=relative dielectric constant $\epsilon_o$=dielectric constant of free space A=area of capacitor plates (sq. meters)

1=spacing between capacitor plates (meters)

Applying this relation to a field cell capacitor with a square end (b=1) results in a capacitance $C_o$ of the field cell as given below:

$$C = \frac{\epsilon \epsilon_o b d}{1} = \epsilon \epsilon_o d \quad \text{(Equation 7)}$$

By dividing by d, we obtain the capacitance per unit depth of a field cell as given below and referred to as the field cell capacitance:

$$\frac{C_o}{d} = \epsilon \epsilon_o \quad \text{(Equation 8)}$$

Using the relationships in Equations 6 and 7, any field cell can be subdivided into smaller square-ended cells with as many cells in parallel as in series. According to Equation 8, the capacitance per unit depth of any field cell, independent of its actual size, which is square or curvalinear square is equal to $\epsilon \epsilon_o$.

The average flux density, D, at the equipotential surface of a field cell can be expressed by the following:

$$D = \frac{Q}{bd} = \rho s \quad \text{(Equation 9)}$$

where:

Q=total charge on foil at equipotential surface of field cell which is equal to total flux $\psi$ through cell, C.

b=width of cell (meters)

d=depth of cell (meters)

$\rho_s$=average surface charge density on the foil at equipotential surface (C/m²)

Hence, the average flux density is inversely proportional to the field cell width. Also, the average surface charge density, $\rho_s$ at the conducting surface is inversely proportional to the width of the field cell at the surface. Since the electric field, E, is defined as the ratio $D/\epsilon \epsilon_o$, the field intensity is also proportional to the cell width or length (i.e., E=V/1 where V is the potential). It has been shown (Kraus, id. p. 166) that the total capacitance, C, for any arbitrary arrangement of conductors separated by electrically insulating material with dielectric constant $\epsilon \epsilon_o$ is given by:

$$C = \frac{N}{n} C_o \quad \text{(Equation 10)}$$

where $C_o$=capacitance in one cell as defined in Equation 7

N=number of field cells in parallel in the region between the conductors n=number of field cells in series in the region between the conductors of the same kind as the ones in parallel.

The above relationships can now be applied to the coaxial conductors illustrated in FIG. 3. By way of example, assume that the radious Ri of the inner conductor is 1.1 units and the radius $R_o$ of the outer conductor is 2.9 units with the inner conductor centerline offset by a distance of 1.1 units from the outer conductor centerline. After partitioning the region between the inner and outer conductors into curvalinear squares of the same kind, we can compute the capacitance using the relationships in Equations 7 and 10 as follows:

$$C = \frac{N}{n} C_o = \frac{N}{n} \epsilon \epsilon_o L \quad \text{(Equation 11)}$$

where

L=is the length of the coaxial conductor and the same as defined for concentric coaxial conductors defined in Equation 1.

Upon inspection of FIG. 3, we find N=16 field cells in parallel and n=4 field cells in series.

Hence, by Equation 11, $$C = \frac{16}{4} \epsilon \epsilon_o = 4 \epsilon \epsilon_o L \quad \text{(Equation 12)}$$

Figure 6:
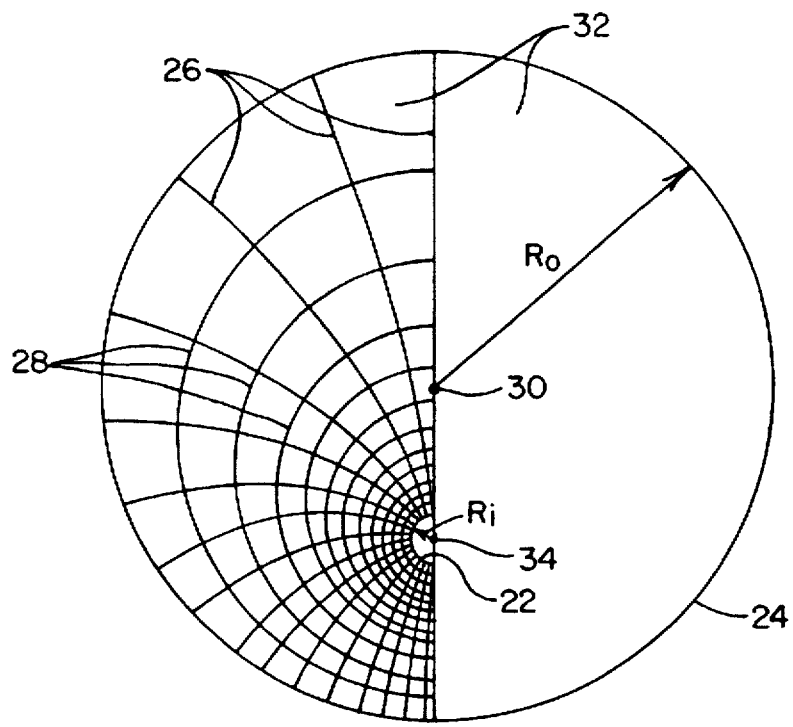
FIG. 6 is a field mapping representation similar to FIG. 3 with an inner conductor representation of smaller diameter.

Referring to FIG. 6, the inner/outer conductor relationship discussed in connection with FIG. 3 is reproduced but with a diminution of the internal radius, Ri, of the inner conductor 22 reduced by a factor wherein it becomes five times smaller than the perimeter of the outer conductor 24, or the outer surface of the electrically insulated dielectric material 32. By reducing the radius of the inner conductor 22 to one-fith of the outer conductor 24 radius, i.e. 0.58 units, the capacitance is reduced proportionally to the larger number of field cells that are in series between the conductors. By the present illustration, the number of field cells in a series (N) has been increased from 4 to 12, and the capacitance is given by:

$$C = \frac{N}{n} \epsilon \epsilon_o L = \frac{16}{12} \epsilon \epsilon_o L = 1.33 \epsilon \epsilon_o L \quad \text{(Equation 13)}$$

Figure 7A:
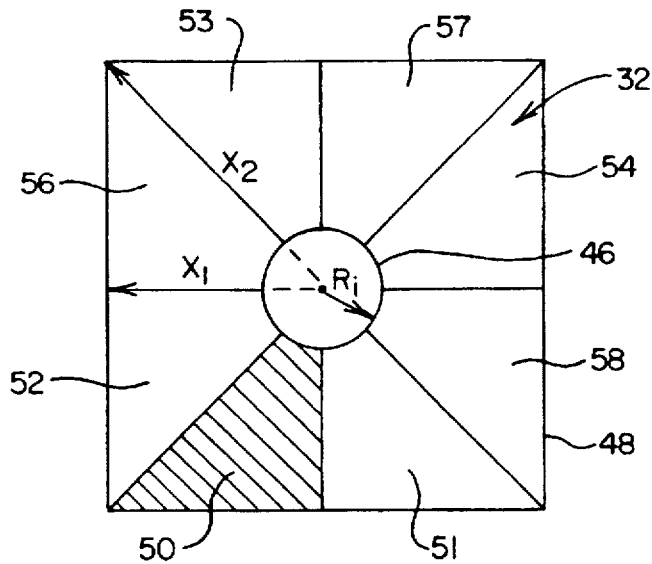
FIG. 7A is an analytic representation of a conductor arrangement according to the invention with arbitrary perimeters.
Figure 7B:
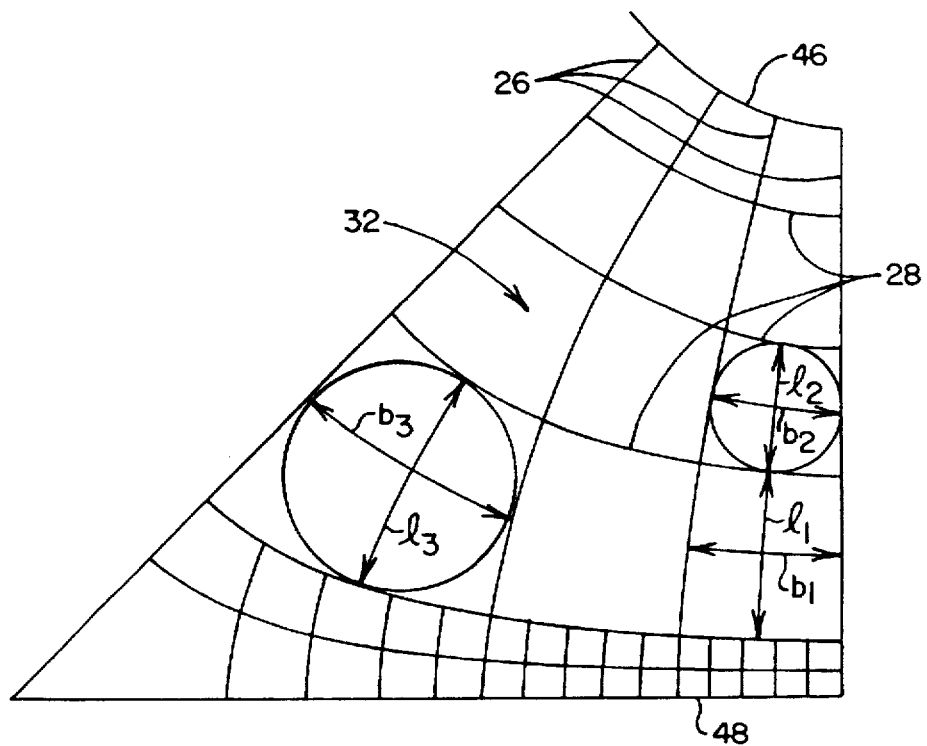
FIG. 7B is an enlarged sector taken from FIG. 7A.

Hence the capacitance has been decreased from 4.0 $\epsilon \epsilon_o L$ to 1.33 $\epsilon \epsilon_o L$ or by a factor of 3 by decreasing the radius of the inner conductor from 1.1 units (in FIG. 3) to 0.58 units (in FIG. 6). Likewise, the field mapping technique can be applied to other arbitrary arrangements of inner and outer conductors such as is shown in FIG. 7A. As before, the arrangement of inner conductor 46 and outer conductor 48 shown in FIG. 7A can be first divided into the smallest sector of symmetry, viz, sector 50 shown in shaded fashion. Corresponding sectors 51–54 are mirror images of sector 50, while sections 56–58 are like or duplicates thereof. Sector 50 can then be further subdivided into a multiplicity of curvalinear squares, maintaining at all locations the required orthogonality between field lines and equipotential surfaces. By partitioning sector 50 according to the prescribed method, a field map is obtained as illustrated in FIG. 7B. Using the relationship presented above in Equation 10, the capacitance can be computed as follows and using the known relationship that the capacitance of capacitors $C_1$, $C_2$ ... $C_m$ in series is given by:

$$C = \frac{1}{C_1} + \frac{1}{C_1} + \ldots + \frac{1}{C_m} \quad \text{(Equation 14)}$$

For the two regions of the sector in FIG. 7B which can be treated as capacitors in series, the total capacitance is given by:

$$C = \epsilon \epsilon_o L \frac{N}{n} = \epsilon \epsilon_o L \left[ \frac{1}{\frac{1}{\frac{N_1}{n_1}} + \frac{1}{\frac{N_2}{n_2}}} \right] \quad \text{(Equation 15)}$$

-continued $$C = \epsilon\epsilon_o L \frac{1}{\left[\frac{1}{\frac{3}{4}}\right] + \left[\frac{1}{\frac{15}{2}}\right]} = \epsilon\epsilon_o L(0.68) \quad \text{(Equation 16)}$$

From the foregoing, it may be observed that by reducing or pulling in the perimeter or radius of the inner conductor 46 and/or by increasing or pushing out the perimeter or size of the outer conductor 48, additional field cells are added between the equipotentials defined by those inner and outer conductors. As a consequence of the relationship shown in Equation 15, or more generally in Equation 11, the larger the value of n (i.e. the larger the number of field cells in series between the inner and outer conductors) relative to the value of N (i.e. the number of field cells in parallel), the smaller the value of capacitance. Furthermore, the smaller the capacitance between the inner and outer electrically conductive members, the lower the current flow by capacitive coupling (see Equation 4) and the lower the level of hazards to the patient or user associated with capacitive coupling. In view of the above it may be observed that the capacitance between two conductive members can be reduced by one or more of the following measures: maintaining the radius or perimeter of the inner conductive member as small as possible relative to that of the outer conductor, preferably maintaining the ratio of the outer perimeter (or radius) to the inner perimeter (or radius) greater than 2 and more preferably greater than about 4; locating the center line of the inner conductor as close to the center line of the outer conductor as possible so that the dielectric media is distributed as uniformly as possible between the two conductors; and using a relative dielectric material having the lowest possible dielectric constant, less than a value of about seven. In general, this relative dielectric constant should fall within a range of about 2 to 7.

To achieve the benefits of the instant invention in connection with the discussion set forth in connection with FIGS. 1, 3, 6, and 7A above, it is important to recognize that no passive electrical coating or similar member (e.g. an outer metallic shaft as in conventional instrument construction) should be located peripherally outwardly from the inwardly disposed electrically conductive member. Any such electrically conductive external member, such as a metallic shaft over the outer surface of a thick-walled electrically insulating material, would function as a "collector" (i.e., the other half of a capacitor) and would collect capacitively induced charge. This is to be avoided. If any localized region along the length of the outer conductive member would contact tissue (e.g. bowel), all of the collected charge over the entire length of the outer conductive member would be transferred to the contactive tissue in the form of a brief, concentrated current flow which can cause unwanted thermal damage to the tissue in contact therewith.

By contrast, in accordance with the teachings of the present invention, the avoidance of any electrically conductive member along the length of the shaft of the instrument (other than the small diameter electrically conductive lead wire leading to the tip) prevents any such "collection" over a distributed region and possible concentration at a localized point of contact with tissue. Consequently, the only capacitively coupled current which can flow to tissue with the present invention is limited by the area of tissue in contact with the electrically insulating shaft, under the assumption that this is an electrically conductive interface forming a second capacitor component or plate. For such topology, capacitive coupling (for a given frequency and voltage) is a localized effect dependent only on (1) the relative radius of the outer shaft surface in contact with tissue and the radius of the inner electrically conductive member, (2) the area of the tissue in contact with the surface of the outer shaft, and (3) the dielectric constant of the intervening electrically insulative member.

Figure 8A:
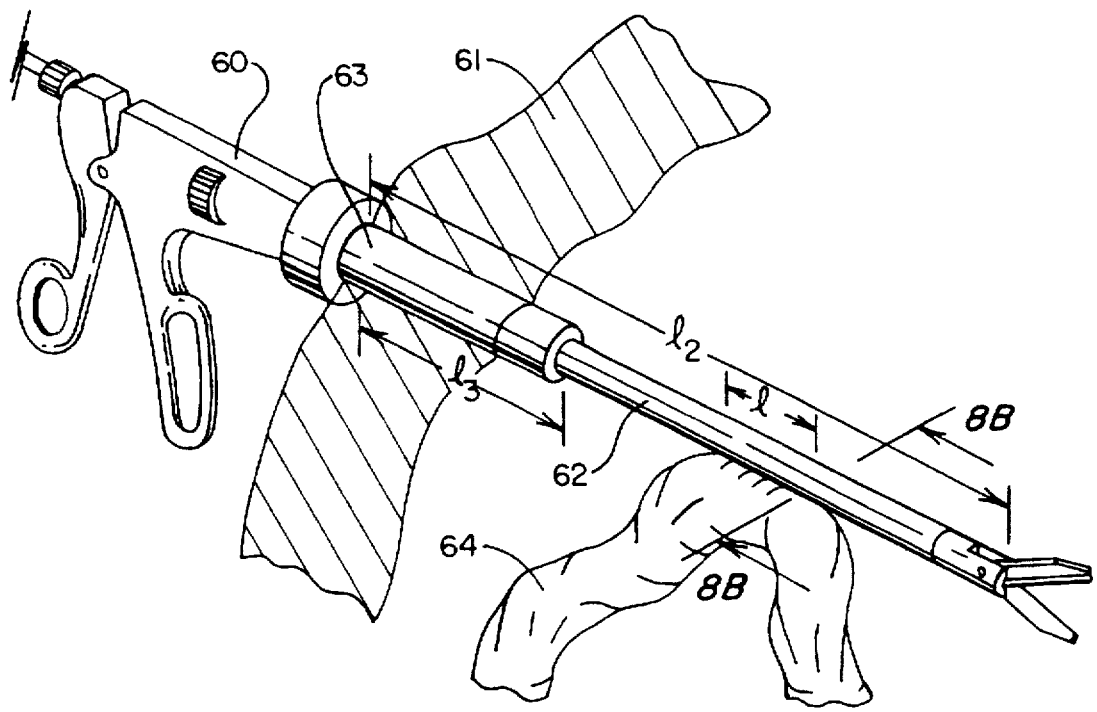
FIG. 8A is a pictorial representation of a monopolar surgical device having a shaft inserted through a cannula, which in turn, has been positioned through an abdominal wall.
Figure 8B:
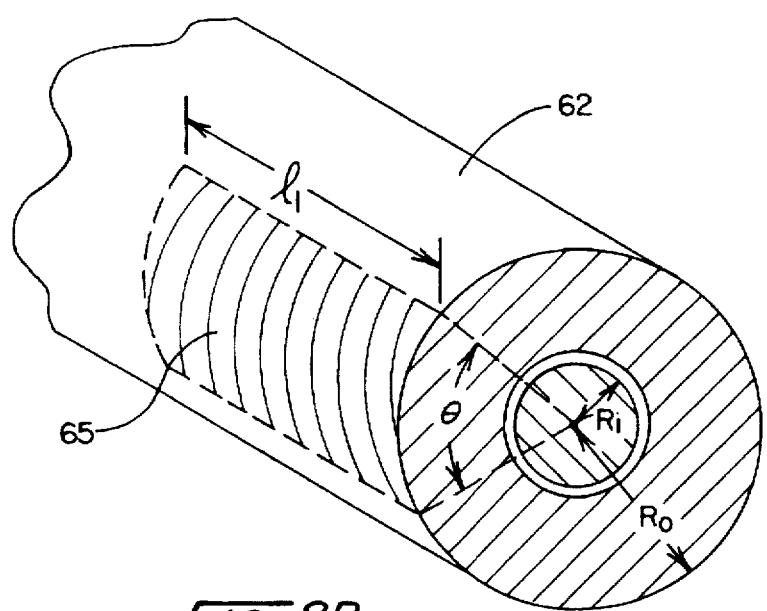
FIG. 8B is a sectional, pictorial representation of a portion of the shaft of the instrument depicted in FIG. 8A, taken through the plane 8B—8B and additionally showing geometric parameters.

This feature of the invention is exemplified in FIGS. 8A and 8B. In FIG. 8A, a laparascopic monopolar electrosurgical instrument is represented generally at 60. Instrument 60 is illustrated in a manner showing its relationship to and penetration through the abdominal wall 61 of a patient. Additionally revealed in the drawing is the position of the shaft 62 of such an instrument as it is located within a cannula 63 which will have been inserted by the surgeon through the abdominal wall 61 using a trochar or the like. Note that the cannula 63 surrounds a portion of the overall length of the shaft 62 of instrument 60. It may be assumed that a small fraction of the length of shaft 62 comes into contact at its perimeter with an anatomical structure 64 (e.g., bowel) in the course of surgical procedure. It may be assumed, for example, that the anatomical structure 64 contacts the perimeter of shaft 62 over a relatively small length, $l_1$, with respect to the overall length, $l_2$, of the shaft 62. For further illustration, it may be assumed that the shaft 62 extends through the tube or guideway of cannula 63 which, in turn, has a length designated as $l_3$. Looking additionally to FIG. 8B, the region of contact of shaft 62 with structure 64 is geometrically illustrated in conjunction with a circumferential arc defined by angle $\theta$ (in degrees) over the noted length, $l_1$.

With the arrangement thus depicted, any capacitive coupling which can occur between the shaft 62 of instrument 60 and the anatomical structure 64 will be limited, for example, as follows:

1. As noted in conjunction with equations 1 and 4 above, the maximum current that can flow is minimized by making the effective radius, $R_i$, of the inner conductor much smaller than the effective radius, $R_o$, of the outer perimeter of shaft 62.

2. Capacitive coupling is reduced still further by the fact that only a fraction of the circumference and total length of the shaft 62 is in contact with a peripheral area shown in FIG. 8B at 65 having a length, $l_1$, and subtending the solid angle $\theta$. Because the small diameter inner electrically conductive member is substantially spaced inwardly from the area of contact 65, the capacitive coupling and associated capacitive current is limited to that based upon the physical area 65 in close proximity or in contact with tissue or anatomical structure 64. From the standpoint of current collection, it should further be borne in mind that the contact at area 65 generally would be of relatively small duration, for example, as compared with the more continuous collection which might be associated with an outer conductive surface extending along the entire length, $l_2$, of shaft 62. For the case of a concentric, circular inner conductor of radius $R_i$, and the electrically insulative principal component of shaft 62 with a periphery of radius, $R_o$, the capacitance is given, according to equation 1, as follows:

$$C = \frac{2\pi\epsilon\epsilon_o l_1}{\ln(R_o/R_i)} \cdot \frac{\theta}{360} \quad \text{(Equation 17)}$$

If $\theta$ were 36°, then the capacitive coupling would be only approximately one-tenth of that value corresponding to the case where the entire circumference is in contact with an electrically conductive medium (e.g. anatomical structure 64). By contrast, were shaft 62 surrounded over its entire length, $l_2$, by an electrically conductive member (e.g. a stainless steel outer tube), then the capacitive coupling and associated capacitive current which can flow between shaft 62 and the anatomical structure 64 is given, according to equation 1, as follows:

$$C = \frac{2\pi\epsilon\epsilon_o l_2}{\ln(R_o/R_i)} \cdot \frac{360}{360} \qquad \text{(Equation 18)}$$

where $l_2$ is much greater than $l_1$, and θ is a complete circumference, i.e. 360°. Accordingly, the capacitance and associated capacitive current will be hundreds of times larger than if no electrically conductive member is present exterior to the inner electrically conductive member.

3. With continuing reference to FIGS. 8A and 8B, in the event an electrically conductive cannula 63 is used, capacitive coupling will be given according to Equation 1 as follows:

$$C = \frac{2\pi\epsilon\epsilon_o l_3}{\ln(R_o/R_i)} \qquad \text{(Equation 19)}$$

The condition thus evolved is not substantially different than if electrically conductive tissue within abdominal wall 61 were in direct contact with the outer periphery of shaft 62. The amount of capacitive coupling and associated current that can flow will be limited by the maintenance of the radius, $R_i$, to values which are quite small with respect to the radius, $R_o$, of the outer surface of shaft 62. Also, the intimate electrical contact between the abdominal wall 61 and the cannula 63 (or even the shaft 62 if no cannula 63 were used) serves to distribute the limited capacitive current which does flow between the shaft 62 and abdominal wall 61 such that no injury occurs to the patient.

4. To limit conductivity, it is desirable to reduce the possibility that a thin, electrically conductive layer of fluid (e.g. physiological saline irrigant or blood) could collect on the surface over a significant portion of shaft 62. This would cause the shaft to behave as a collector resulting in greater capacitive coupling. To avoid such a condition, the outer peripheral surface of shaft 62 should be smooth and resistant to "wetting" by saline solution or blood. This may be accomplished, for example, by selecting a shaft material which has non-wetting characteristics to saline solution or blood (e.g. polytetrafluoroethylene compounds) or by applying a coating to the outer surface of shaft 62 which exhibits non-wetting characteristics to saline solution or blood (e.g. polytetrafluoroethylene coating). As a result of the non-wetting characteristics of the shaft material or coating on the shaft, any electrically conductive fluid in contact therewith will form small droplets or "beads" of liquid which will interrupt the electrical continuity otherwise required for such liquid deposits to behave in concert as an extended conductive surface collector. Accordingly, it is desirable that the shaft exhibit a substantially hydrophobic characteristic.

Referring to FIG. 9, a monopolar electro-surgical system for laparascopic/endoscopic application is represented generally at 70. System 70 includes a multiple function electrosurgical instrument 72 which performs, inter alia, an electrosurgery generator 74 by virtue of its connection therewith through a lengthy flexible cable 76. While the generator 74 provides conventional electrical surgical current output at conventional frequencies, it is shown interfaced with an adapter 78 located intermediate the cable 76 and device 74. Adapter 78 will be seen to be employed with a shield containing embodiment of the invention. In using the generator 74, the surgeon makes adjustments, for example, as provided at control knobs 80 and 82, to carry out a cutting mode, for example at potentials of about up to about 2000 V, or a coagulation mode of much higher levels, for example up to 6000 V. Generally, these parameters include high frequencies of 200 kHz and higher. Application of currents from generator source 74 typically are from a foot pedal control as at 80 providing a switched signal to device 74 via cable 86.

Inasmuch as instrument 72 performs in monopolar fashion when inserted within the patient, the patient, in turn, is positioned upon a return electrode 88 which is seen coupled via cable 90 with the generator 74 through connector 422.

Instrument 72 is formed having an elongate shaft 92 of diameter selected for insertion through a trochar-formed opening in the body of the patient which is maintained through the utilization of a cannula. Shaft 92 is formed having a working end 94 which may carry a variety of instrumentalities, here that instrumentality being selected as a scissors pair 96 having cooperating blades 98 and 100. Blades 98 and 100 are formed of a metal and are mounted for pivotal movement about a pivot 102 mounted, in turn, within a working end housing 104 which is of the same diameter, for example, as shaft 92. Actuation of the blades 98 and 100 of scissors 96 is by an internally disposed driveshaft (not shown) which is moved reciprocally by the surgeon from the grasping end 106 of shaft 92 which is mounted within and supported by a handle housing 108. Housing 108 includes a stationary finger loop 110 arranged for grasping by hand of the surgeon in conjunction with a movable finger loop 112 forming part of a drive lever 114 pivoted to housing 108 at a pivot connector assembly 116. Relative movement between the finger loops 110 and 112 as carried out by the surgeon provides for the corresponding generally reciprocal movement of the upper or drive portion 118 of drive lever 114 to, in turn, drive the noted driveshaft, in turn, actuating scissors 96. To afford additional operational flexibility of the instrument 72, the shaft 92 thereof may be manually rotated by the surgeon by rotation of a finger knob 120. Where it is desired to coagulate or carry out an electrosurgical transection or cutting from the metallic scissors 96, current from the generator 74 is applied in response to actuation of pedal 84 through cable 76 and into instrument 72 through a connector 122.

Figure 10:
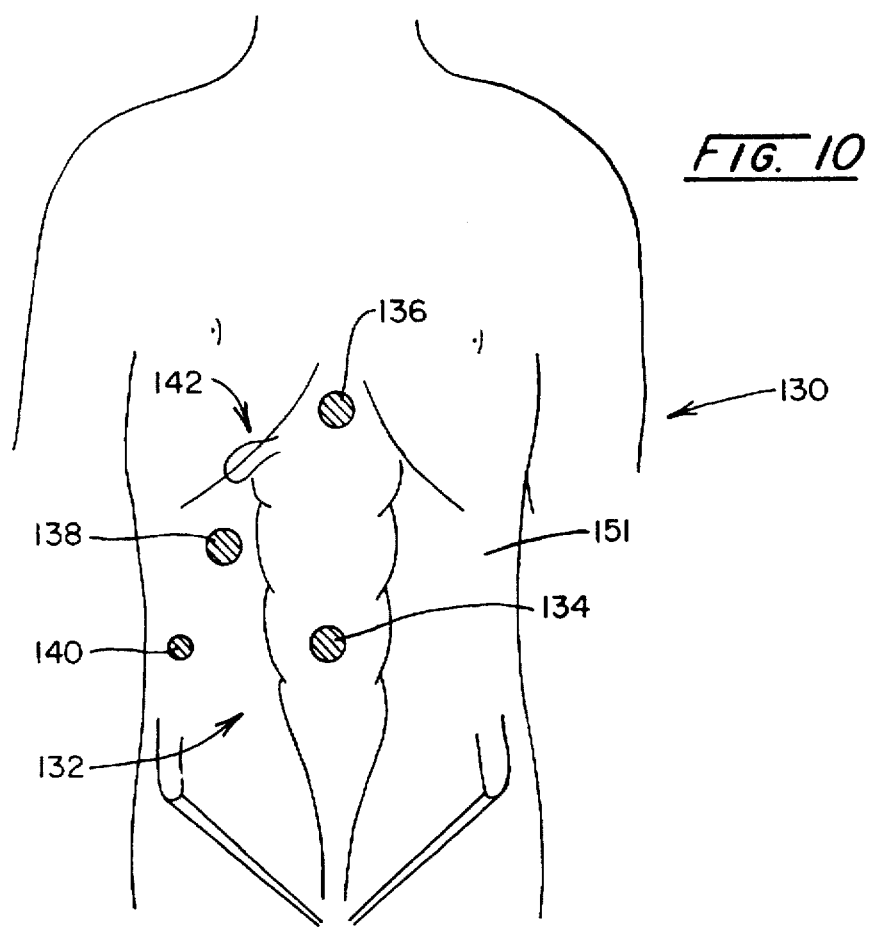
FIG. 10 is a ventral plan view of the abdomen of an insufflated patient showing the location of cannula ports for a laparoscopic cholecystectomy surgical protocol.

Instruments 72 are provided in a number of configurations. In some of those configurations, the instruments or portions of them, are made disposable for one-time use to avoid the difficulties otherwise associated with cleaning and sterilizing. Alternately, the devices may be wholly or partially reusable. In the course of their normal use, however, the devices including working end 94 and shaft 92 are inserted within the human body. For example, the laparoscopic approach to cholecystectomy commences with insufflation of the peritoneal cavity of the anesthetized patient. Typically, this expansion of the cavity (pneumoperitoneum) is carried out by the controlled insertion of an insulating agent such as carbon dioxide through a supraumbilically inserted Verres needle. That needle is operatively associated with an insufflator machine, usually providing a pressure and flow rate control over the insufflating agent. A sequence of cannulas are placed into the peritoneal cavity using sharp, removable trochars. These cannulas are valved devices through which a video imaging camera and light source along with instruments such as described at 72 can be passed and manipulated from outside the patient's body during the procedure. The cannulas will vary in port diameter, ranging for instance, from 5 mm to 18 mm. Looking to FIG. 10, the ventral view of an insufflated patient is schematically represented at 130 as positioned for intra-abdominal access to the peritoneal cavity 132. To carry out a laparoscopic cholecystectomy procedure, a number of cannular ports are provided which are depicted in the drawing. These ports include an umbilical port 134, an epigastric port 136, and mid-clavicular port 138 may be provided as having, for example, 10 mm port diameter while an interior auxiliary port 140 may be provided as having a 5 mm port diameter. The number, the port diameter size, and the location of the cannula is used to access the location of the gall bladder as represented at 142, may vary depending on such factors as the body habitus of the patient and the internal structure of the biliary anatomy. As is apparent, electrosurgical instruments employed in this procedure may approach and come in contact with organs and tissue other than that targeted for transection and the like. Where stray capacitance based currents occur, substantial damage may be done to such organs or tissue, such occurrences often taking place out of camera view.

Figure 11:
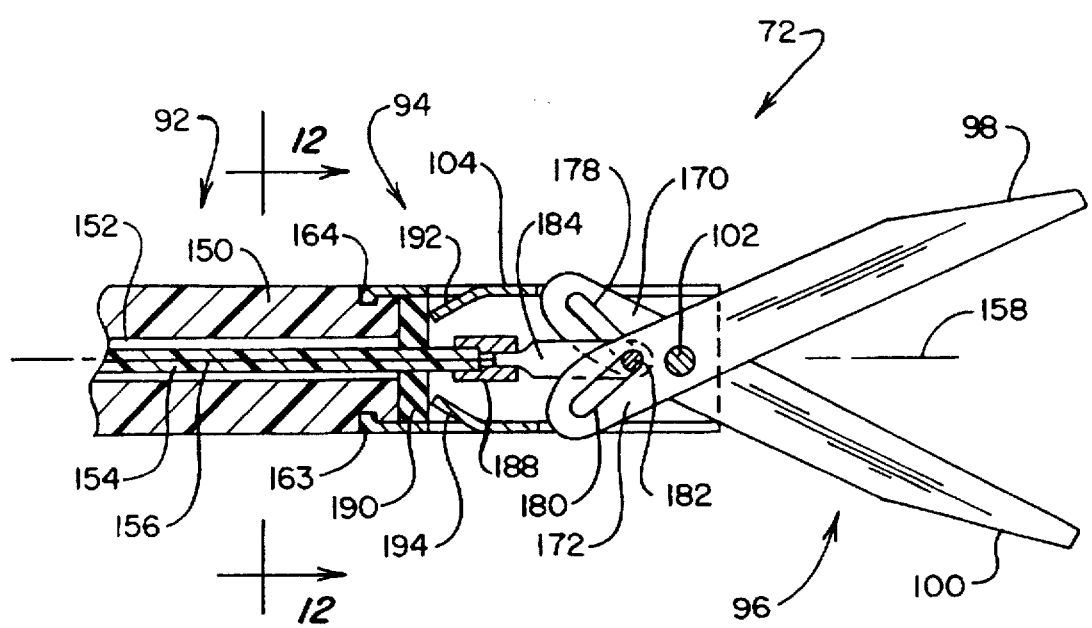
FIG. 11 is a sectional view of the working end of an electrosurgical instrument shown in FIG. 9.
Figure 12:
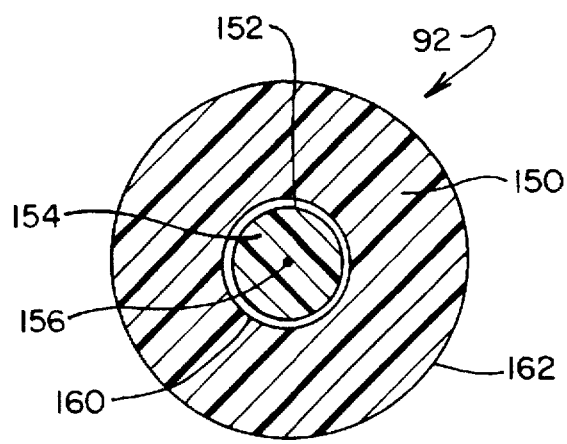
FIG. 12 is a sectional view taken through the plane 12—12 shown in FIG. 11.

Looking to FIG. 11, the internal structure of shaft 92 at its working end 94 supporting scissors 96 is revealed in enhanced detail. In accordance with the invention, the shaft 92 is formed principally of an electrically-insulating material of low dielectric constant at working frequencies in the range from about 200 KHz to 4 MHz. For the embodiment of FIG. 11, the shaft is formed as an elongate cylinder formed of polymeric material as is represented at 150. Within the shaft 92 there is formed a cylindrical cavity 152 which extends throughout its length. The drive rod or driveshaft for actuating scissors 96 is provided as a cylindrical rod 154 formed of the same type of electrically insulating, low dielectric constant material. However, to conduct current for electrosurgical purposes to the scissors assembly 96, a thin electrically conductive wire 156 is embedded along the central axis 158 of the cylindrical driveshaft 154. Wire 156 will have a diameter, for example, of between about 5 to 10 mils (0.2 to 0.4 mm). Preferably, both the driveshaft 154 and the shaft 92 are coaxially disposed about the central longitudinal axis 158. Looking momentarily to FIG. 12, the cross-sectional geometry which results from this structuring of shaft 92 is revealed. With this arrangement, the radius of wire 156 will be about 0.1 to 0.2 mm, while the corresponding radius to the outer surface 162 of shaft 92 will be between about 2.5 to 9 mm disregarding the very low dielectric constant represented by the gap 160 defined by the cavity 152 intermediate drive rod 154 and shaft 92, and considering the outer surface 162 of shaft 92 to be a conductive position in view of its interface or contact with human tissue, the resultant ratio of radii as discussed in connection with curve 20 in FIG. 2 results in a particularly low capacitance factor, $F_c$. Based on Equation 3 and the above dimensions, the capacitance factor, $F_c$, for the present invention ranges from 0.3 for 0.4 for 5 mm diameter endoscopic instruments; for 10 mm diameter endoscopic instruments, the capacitance factor $F_c$, for the present invention ranges from 0.26 to 0.31. This capacitance factor of the present invention is accordingly as much as 75 times smaller than that for conventional endoscopic electrosurgical instruments. Material suitable for the outer shaft 50 as well as the driveshaft 154 may be: polyether ether ketone sold under the trade designation "PEEK", for example by Vitrex Corp. which exhibits a dielectric constant of 3.2 to 3.5 and may be employed for single use instruments or for autoclavable or reusable instruments; polyether sulfone sold under the trade designation "RADEL 5100-NT15" by Amoco Performance Plastics of Alpheretta, Ga., which exhibits a dielectric constant of 3.4 and may be employed for either single use or is autoclavable (the preferred material); polyarylether ketone sold under the trade designation "ULTRAPEK" and marketed by BASF Corporation-Plastic Materials, Parsippany, N.J., exhibiting a dielectric constant of 3.3 to 3.8 and which is autoclavable or may be employed for single use instruments; polyamide sold under the trade designation "ULTRAMID" by BASF Corporation (supra), exhibiting a dielectric constant of 3.1 and which is suitable for single use; polytetrafluoroethylene sold under the trade designation "TEFLON" and marketed by DuPont Corp. of Wilmington, Del., exhibiting a dielectric constant of 2.0 to 2.2 and which is autoclavable and may be employed for single use or reusable instruments. Other materials which may be employed include homogenous (unfilled) polymeric material; glass (fiber) filled polymeric materials; hollow, electrically insulating microspheres dispersed in polymeric material; ceramic (fiber) filled polymeric material; polyamide; polyethylene; polypropylene; polycarbonate; glass; glass/ceramic; and ceramic materials.

Returning to FIG. 11, and looking additionally to FIG. 13, the working end housing 104 is seen to have a cylindrical shape, the rearward end thereof being formed inwardly at 163 so as to provide a snap-in or press fit within a groove 164 formed within working end 94 of shaft 92. Upper and lower aligned slots of rectangular shape are provided at 166 and 168 for the purpose of accommodating the movement of scissor blades 98 and 100. These blades 98 and 100, respectively, extend rearwardly to respective shank portions 170 and 172. Shank portions 170 and 172 are each formed having a pivot hole shown, respectively, at 174 and 176 (FIG. 13) through which the pivot pin 102 extends. Additionally, shank portions 170 and 172 are formed having respective elongate slots 178 and 180 which receive a drive pin 182. Drive pin 182 is slidably retained within the slots 178 and 180 and is attached to a blade coupler 184 at a hole 186 formed therein. Coupler 184 as well as drive pin 182 are formed of an electrically conductive metal. The coupler rearward portion is fixed to an electrically insulative connector 188 which additionally is fixed to the end of drive rod 154. In this regard, current is conveyed to the scissors assembly 96 through the blade coupler 184 which, in turn, is coupled to the conducting wire 156 at the insulative connector 188. Thus, a fragile conductor of minimal radius is employed only to convey current to the blade structure 96, while the insulative driveshaft 154 carries out the duty of actuation of the scissors assembly 96.

To limit the ingress of contaminants such as body fluids and the like toward the shaft 92, a gasket 190 is positioned within working end housing 104 adjacent its rearward end 162 and with a slidable fit over drive rod 154. Gasket 190 is retained in place by detents 192 and 194 formed inwardly from the surface of housing 104.

Figure 14:
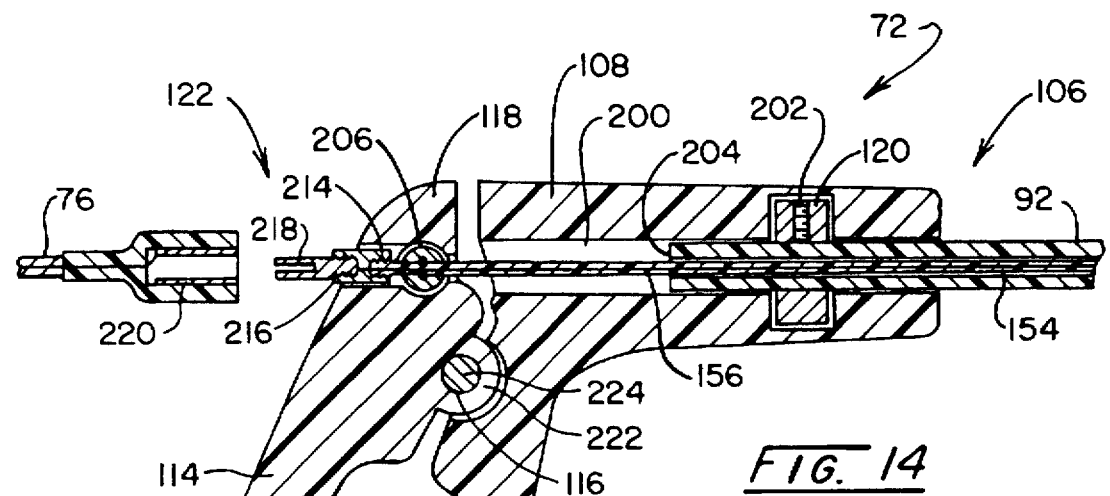
FIG. 14 is a partial sectional view of the grasping end of the electrosurgical instrument shown in FIG. 9.
Figure 14A:
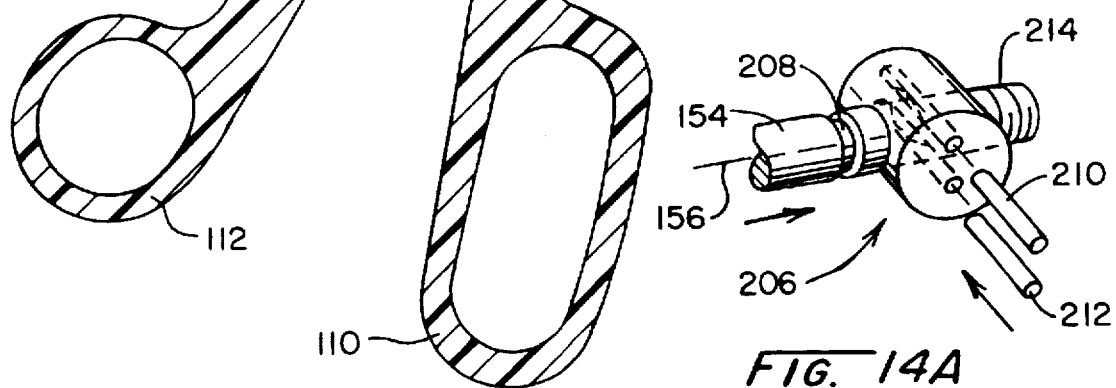
FIG. 14A is an enlarged, partial perspective view of a drive shaft connector comprising a cylinder and pin assembly shown in FIG. 14, depicting assembly arrows.

Turning to FIG. 14, the grasping end 106 and associated handle housing 108 of instrument 72 are revealed at an enhanced level of detail. Shaft 92 is seen to be positioned within a cylindrical cavity 200. Rotation of the shaft 92 is permitted by this retention within cavity 200 and the shaft is retained or captured within the housing for this rotation by finger knob 120 which is fixed thereto by a set screw 202. Note that the driveshaft 154 extends outwardly from the rearward end 204 of shaft 92, whereupon it is coupled to the upper portion 118 of drive lever 114 by a cylinder and pin assembly 206. In this regard, and looking additionally to FIG. 14A, the cylinder 206 is formed having an opening extending essentially horizontally therethrough which receives the driveshaft 154. Driveshaft 154, in turn, is formed having a circumferential groove 208 which is captured by two parallel pins 210 and 212 extending longitudinally through the cylinder 206. With that arrangement, the driveshaft 154 is fixed to upper portion 18 of drive lever 114 while being permitted to rotate in conjunction and correspondence with the rotation of shaft 92. Driveshaft 154 additionally is seen to extend through the cylinder 206 to an end at 214 which is attached to a connector 216 forming a portion of connector 122. Wire conductor 156 also extends into connector 216 and is coupled to an active electrode terminal 218. Terminal 218 is manually connectable with a corresponding female connector terminal 220 which forms a termination of cable 76. With the arrangement shown, the terminal 218 as well as connector 216 will rotate as shaft 92 is rotated. This, in turn, will cause rotation of the connector 220 and cable 76. However, because of the length of cable 76, the extent of torsion involved is minimal. While for the embodiment shown, the assembly 206 may be formed from either electrically insulative or conductive materials, for embodiments where the driveshaft is conductive, then an insulative material would be used.

Pivotal connection 116 is of a conventional variety, the drive lever 114 being formed having a circular pivot component (not shown) which slidably is received within a slot formed within a cylinder 222 integrally formed with the handle housing 108. A pivot pin 224 completes the assembly.

As is apparent, the instrumentation to which the invention is applied may take on a variety of forms. For example, components utilizing driveshaft actuation and the like may be employed with graspers as well as scissors. While the scissors embodiment generally will employ coagulation voltage and frequency values, a grasper for example, may be employed for cutting purposes at different electrical parameter values.

Referring to FIG. 15, another instrument which may be employed with the system 10 is shown at 230. Device 230 is a fixed tip electrosurgical instrument which employs an elongate shaft 232 having a working end 234 to which a cutting or incising component (e.g. hook shaped components)236 is attached. In this regard, element 236 is formed of conductive metal and includes a cylindrical support portion 238 coupled to the tip 240 of shaft 232 through the utilization of a press fit form of connection or using suitable adhesive materials.

Shaft 232 is formed of the above-identified materials suited for earlier-described shaft 92. Looking to the sectional view of shaft 232 shown in FIG. 16, it may be observed that a cavity 242 of generally circular cross-section is formed within the shaft 232 within which is received a thin wire conductor 244. FIG. 15 shows this conductor to extend from the tip 240 of shaft 232 to a connection at 246 with cutting component 236. The center of cavity 242 as well as wire 244 is slightly off axis with respect to the center axis of shaft 232 in order to accommodate an irrigation/aspiration channel 248 extending along the shaft 232 with a forward opening at tip 240. FIG. 15 shows that the shaft 232 extends rearwardly to a grasping portion 250 which is surmounted by a cylindrical grip 252. In this regard, the shaft 232 is fixed within a corresponding cavity 254 formed within grip 252. The rearward end of grip 252 is configured for supporting a male connector 256 for coupling to cables as at 76 (FIG. 9). The lead from connector 256 at 258 extends through the grip 252 for connection with conductor 244. To provide for irrigtation and aspiration, the channel 248 is connected through a cylindrical fitting 260 to a tube 262 which, in turn, is coupled to an external fitting 264. Fitting 264 may be connected with the hose connector 266 of appropriate irritation/aspiration device.

For the instrument embodiments as at 72 and 230, the adapter 78 described in connection with FIG. 9 is not required. However, for the embodiments to follow wherein a grounded shield is employed, then the adapter 78 is utilized. The electrosurgical embodiment 270 shown in FIG. 17 is one which employs a shaft 272 having a grasping portion 274 retained as before by a handle housing 276. Shaft 272 however, while being formed of a polymeric or other low dielectric constant, electrically insulative material as described above, incorporates a conductive metal shield 278 which is configured substantially as an elongate cylinder and which surmounts elongate centrally disposed cavity 280 which is symmetrically disposed with a circular cross-section about axis 282. Within cavity 280, there is positioned an elongate metal drive rod 284 of conventional variety, for example, having a diameter of about 1.5 mm. Looking additionally to FIG. 18, it may be observed that the shield 278 exhibits a circular cross section and is embedded within the polymeric material of the shaft 272. The diameter of driveshaft 280 is large in comparison to the earlier embodiments. However, by coupling the shield 278 to instrument ground, the effects of capacitive coupling with surrounding tissue and the like are minimized to a level of dismissibility. However, the design should be one which avoids opportunity for decoupling instrument ground and which assures that a proper connection of ground and power source always be made by the user. In general, the shield 278 may be made of a screen-like stainless steel or the like which, for example, in braided form may be coextruded with the polymeric shaft 272. As is apparent, the working connections and the like for the instant embodiment are of conventional structuring, no protection of very small diameter conductors or insulating couplings being required.

Returning to FIG. 17, the shaft 272 is seen to extend within and is supported from a cylindrical cavity 286 formed within handle housing 276. This support from cavity 286 is sufficiently loose to permit rotation of the shaft from a captured thumbwheel 288 retained in connection with shaft 272 by a set screw 290.

Excitation or electro-surgical current is applied to driveshaft 284 of instrument 270 through an electrode coupling shown in general at 304. Coupling 304 includes an externally threaded insulative cap 306 which is threadably retained within a corresponding threaded opening within handle housing 276. That same opening continues as represented at cylindrical opening or bore 309 which extends to and in communication with the cavity 286 retaining shaft 272 and associated drive rod 284. To provide electrical communication between the outwardly exposed electrode connector 314 supported from cap 306 and driveshaft 284, an electrically conductive helical spring and contact rod or brush 308 assembly is provided wherein the contact rod 310 is in physical contact with the surface of drive rod 284 and slidably rides thereupon to accommodate any rotation or longitudinal movement of that latter component.

Positioned adjacent to the coupling 304 is an instrument ground coupling shown generally at 292 which is structured substantially similarly to coupling 304 with differences in dimension. In this regard, the coupling 292 includes an insulative cap 294 threadably engaged within the handle housing 276. Cap 294 retains a conductive spring 300 and a contact rod or brush 302 which extends through an opening to cavity 286. Rod 302 is configured to make positive contact with the screen or braid ground 278. In this regard, the material forming shaft 272 is removed to define a circumferential groove 312 exposing shield material for effective contact with rod 302. Note, additionally, that the upwardly extending electrode connector 314 of electrode coupling 304 is of a different diameter than the corresponding connector 298 of coupling 292. This is for the purpose of assuring a proper union with female connector 316 as seen attached, in turn, to dual lead cable 76 as described in general in connection with FIG. 9. Connector 316 includes a ground electrode cavity 318 configured to nestably receive the connector 298 and an adjacently disposed current conveying electrode cavity 320 which is configured for receiving electrode connector 314. Leads 322 and 323 are seen extending rearwardly from respective cavities 318 and 320, and along flexible cable 76.

To provide for conventional inward and outward actuating movement of driveshaft 284 while assuring contact with contact rod or brush 310, a region of the rod 284 at 326 is provided which terminates in a threaded connection 328 within an electrically insulative cylindrical connector 332. The opposite side of connector 332 is threadably connected to a rod component at 336 and is seen to extend rearwardly along the cavity 286 to a spherical retainer ball component 338 which rides within a cylindrical cavity 340 formed within drive lever 342. Lever 342 is formed having a finger loop 344 and is pivotally coupled at coupling 346 to handle housing 276 which is seen to extend downwardly to provide a stationary finger loop 348. Pivot 346 is configured in the same manner, for example as that shown at 116 in connection with FIG. 14.

In practice, the extent of rotation of shaft 272 is somewhat limited and, employing detents or the like can be restricted to one revolution. Accordingly, the sliding contacts with electrosurgical signal and surgical instrument ground can be replaced with flexible wiring. This permits variations in the structuring of shield containing shafts as at 272.

Referring to FIG. 19, a cross section of such a variation in shaft structuring is revealed generally at 360. Shaft 360 is formed of one of the same polymeric or other electrically insulative materials as described above and has coextruded therewith an embedded shield 362 in the same fasion as shield 278 described in conjunction with FIG. 18. In this regard, the shield 362 may be a coextruded braid or a screen or the like. Shaft embodiment 360 includes cylindrical interior cavity 364 which is coaxially disposed with shaft 360 about axis 366. In this embodiment, however, the driveshaft as shown at 368 is formed of the low dielectric constant, electrically insulative material as described above. Within the driveshaft 368 there is provided a second cavity 370 also symmetrically disposed about the axis 366 within which a conductive wire 372 of very small diameter, e.g. 5–10 mils, is disposed in manner similar to the arrangement described in conjunction with FIGS. 11–14. With this arrangement, should connection with surgical ground be lost with respect to shield 362, capacitive coupling still will be significantly lowered, thereby reducing the potential harm to a patient.

Figure 20:
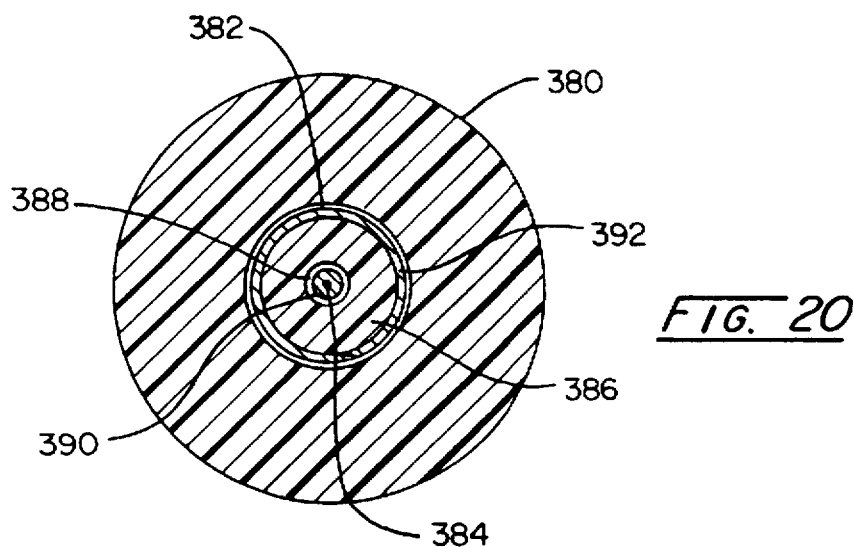
FIG. 20 is a sectional view showing an alternate arrangement for the provision of a shield within a shaft of instruments according to the invention.

Another arrangement for the provision of a shield within the shafts of the instruments is depicted in the cross-sectional arrangement of FIG. 20 at 380. The shaft 380, again being formed of the polymeric or other electrically insulative materials described above, is configured having an inwardly disposed cylindrical cavity which is symmetrical about the central axis of the shaft as represented at 384. Within the cavity 382 there is slidably disposed an electrically insulative cylindrically shaped drive rod 386 which also is disposed symmetrically about the axis 384. A second cavity 388 is formed within drive rod 386 which extends therealong in the manner described in conjunction with FIGS. 11–14 and which carries a thin wire conductor with the same function as set forth in conjunction with those figures. The shield for the arrangement of FIG. 20, however, is provided as a continuous conductive sleeve 392 which is located about the outer surface of drive rod 386. Sleeve 392 may be formed, for example, of stainless steel or may be provided as a thin metal deposition, for example of aluminum having a thickness, for example, of about 0.1 to 0.5 mils.

Figure 21:
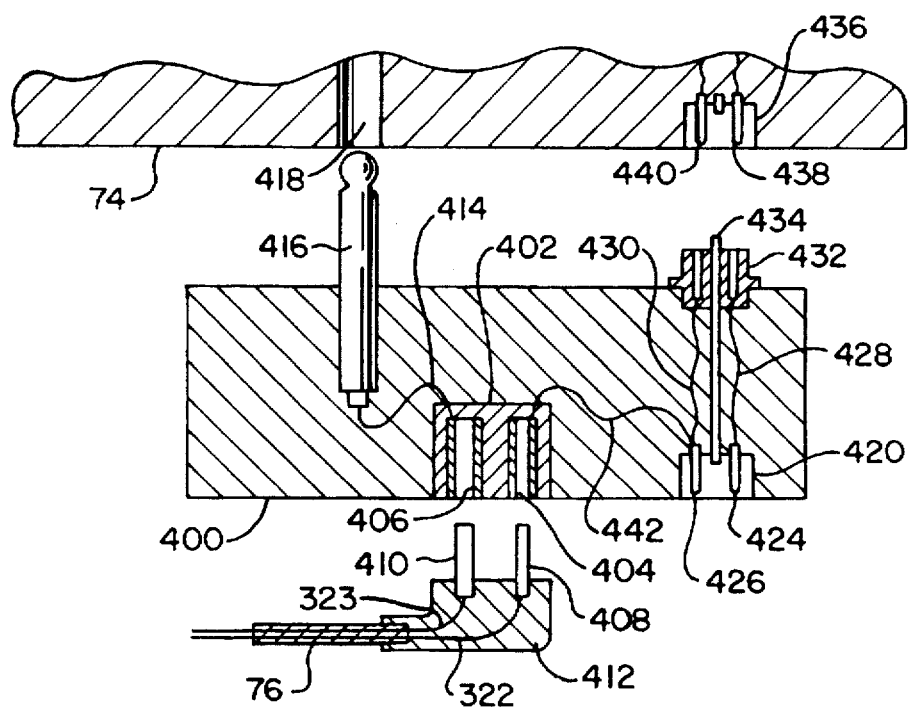
FIG. 21 is a partial schematic and expanded view of an adapter for a surgical generator employed with the invention.

Turning to FIG. 21 and looking again to FIG. 9, the structuring of generator adapter 78 is revealed in enhanced detail. This adapter is employed where shielded shaft configurations are used. Adapter 78 is formed of an electrically insulated polymeric material and the forward face thereof 400 is configured to support a dual electrode electrical terminal 402 which is configured having cavity contacts 406 and 404 corresponding with the respective cavity contacts 320 and 318 of connector 316 (FIG. 17). Accordingly, cavity contact 406 conveys electrosurgical monopolar current signals while the cavity contact 404 connects surgical ground. Shown in association with electrical terminal 402 is a corresponding plug 412 having connectors 408 and 410 configured diametrically for insertion only within respective cavity contacts 404 and 406. Note that the plug 412 is coupled with earlier-described cable 76 carrying leads 322 and 323 reproduced in the instant figure. As before, it is imperative that the terminal 402 and plug 412 be configured so that electrical connection therebetween cannot be reversed.

Cavity contact 406 is seen coupled by a lead 414 to a conventional monopolar plug 416 which is received in conventional fashion within a monopolar receptacle 418 mounted within electrosurgery generator 74.

As described in conjunction with FIG. 9, instrument ground is coupled via a cable 90 to a patient return electrode 88. That cable 90 is connected with generator adapter 78 to an electrical terminal 420 located at the forward face 400. FIG. 9 shows a plug connector 422 to be employed for cooperative insertion within connector 420. That connector will carry two ground components from the patient return electrode 88 for purposes of assuring proper grounding of the patient. Accordingly, the electrical terminal 420 is configured having two male prong contacts 424 and 426 which are coupled by respective leads 428 and 430 within adapter 78 to a mounted plug 432 which is configured identically with plug 420. An alignment rod 434 facilitates the connection of dual terminal female plug 432 with a corresponding dual prong type terminal receptacle 436 formed within the generator 74. In this regard, the receptacle 436 includes two ground prong type terminals 438 and 440. Prong type terminal 426 of receptacle 420 also is tapped by a lead 442 which, in turn, is coupled to the contacts 404 of receptacle 402. Thus, instrument ground may be conveyed to the electrical surgical instrument coupled to cable 76 and plug 412.

Figure 22:
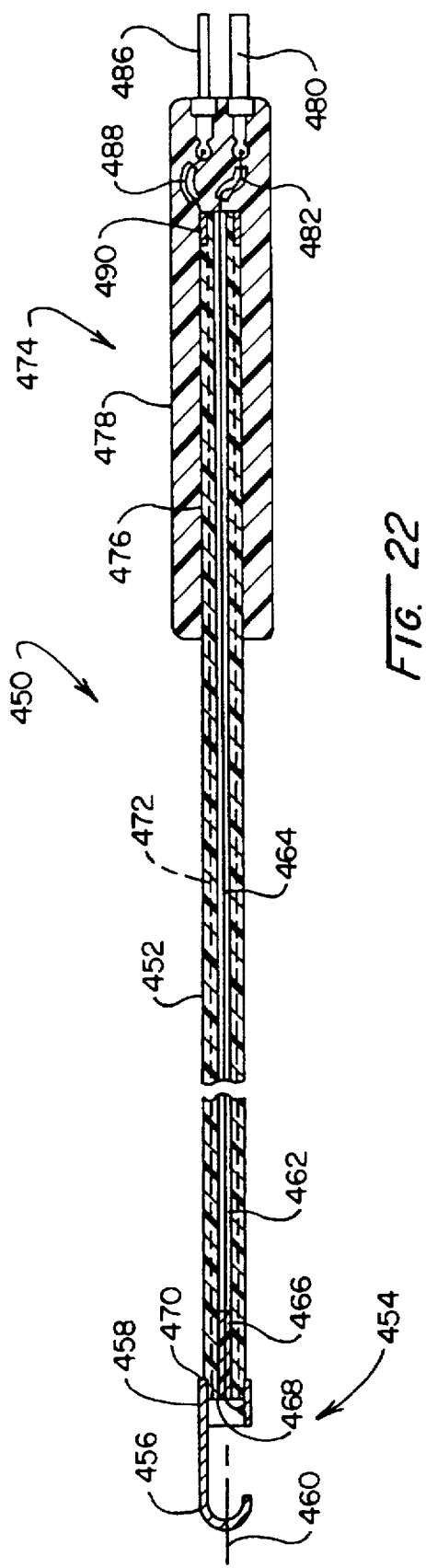
FIG. 22 is a sectional view showing a fixed tip electrosurgical instrument according to the invention.

Referring to FIG. 22, a fixed tip electrosurgical instrument 450 is depicted incorporating a shaft 452 with a shield implementation. The working end 454 of shaft 452 supports a cutting component 456 which serves as a stationary electrode tip (e.g. hook shape) with the same function as that described at 236 in conjunction with FIG. 15. Component 456 is integrally formed with a collar or cylindrical support portion 458 which extends over and is supported by shaft 452. Extending symmetrically along the central axis 460 of cylindrical shaft 452 is a cavity 462 within which is located a thin wire conductor 464. Conductor 464 may be formed having a diameter, for example 5–10 mils, and extends through a seal or plug 466 within cavity 462 through the tip face 468 of shaft 452 whereupon it is coupled electrically with collar 458 of the tip 456. Collar 458 may be coupled to the working end of shaft 452 by a mechanical interface fit which may include, as before, a circumferential groove and detent configuration at 470.

Additionally located within the shaft 452 symmetrically about axis 460 is a braided or screen-like metal shield 472 which surrounds the conductor 464. As before, shield 452 if of a braided configuration, may be coextruded with the insulative low dielectric constant material from which the shaft 452 is formed. Materials for so forming the shaft 452 are described hereinabove. The grasping end of shaft 452 is inserted within the cylindrical cavity 476 of a grip 478. Grip 478, in addition to supporting the shaft 472 for gripping by the surgeon, additionally supports a prong-type terminal 480 which is coupled by lead 482 to conductor 464 and a second prong type terminal 486 of lesser diameter than terminal 480 which is coupled via lead 488 to a cylindrical connector 490 attached to the cylindrically formed shield 472.

Figure 23:
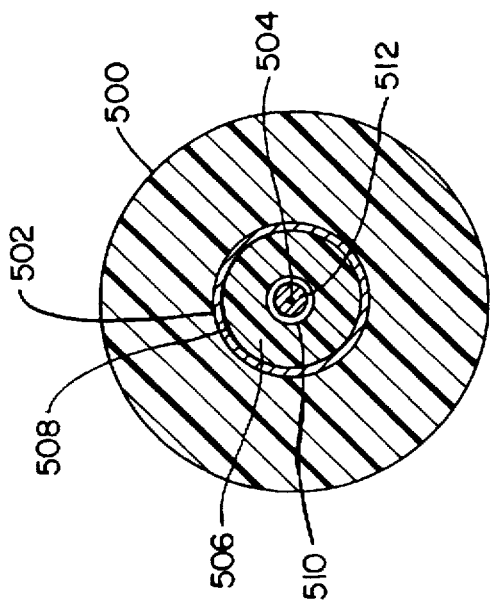
FIG. 23 is a sectional view of another embodiment of a shaft structure according to the invention which may be employed with a fixed tip electrosurgical instrument.

Turning to FIG. 23, an alternate arrangement for the shaft component of instruments such as at 450 is represented in cross-section at 500. Formed of the earlier-described materials, shaft 500 is cylindrical and incorporates an interior cylindrically shaped cavity 502 which is formed symmetrically about the shaft axis represented at 504. Within cavity 502 and arranged symmetrically about axis 504 is a cylindrically shaped, stationary insert 506. The outer surface of insert 506 is provided having a sleeve or coating 508 which is provided in the same manner as that at 392 discussed in conjunction with FIG. 20. Sleeve or coating 508 then functions as the shield for the embodiment of the figure. A second cavity 510 of cylindrical configuration and arranged symmetrically about axis 504 extends along the lengthwise extent of insert 506 and serves, as before, to carry a thin wire conductor 512. With the arrangement shown, by adhesively retaining the insert 506 within the cavity 502, a continuous shield may be provided with the advantageous utilization of a wire conductor 512 of very small diameter, for example 5–10 mils.

Since certain changes may be made in the above apparatus and system without departing from the scope of the invention herein involved, it is intended that all matter contained in the above description or shown in the accompanying drawings shall be interpreted as illustrative and not in a limiting sense.

I claim:

1. An instrument for carrying out monopolar electrosurgical procedures upon tissue within a body in contact with a return ground by insertion of said instrument through minimal size openings to access said tissue, comprising:

an elongate shaft of length along a given axis suited for accessing said tissue, having a working end, a grasping end and an exterior surface of configuration exhibiting a first principal cross-sectional dimension permitting the slidable insertion thereof through said opening into said body, said shaft being formed of an electrically insulative material;

an electrically conductive working tip assembly supported at said working end responsive to an applied current at predetermined frequency for surgical application thereof to select portions of said tissue;

an electrical terminal supported at said shaft grasping end, having an input connectable with a source of said current and an output;

an electrical conductor supported within said shaft, extending therealong in current transfer communication between said electrical terminal output and said working tip and having a second principal cross-sectional dimension substantially less than said first principal cross sectional dimension selected as effective to convey said applied current to said working tip and to lower capacitive coupling between said conductor and said tissue adjacent said exterior shaft surface to an extent substantially atraumatic to said adjacent tissue; and an electrically conductive shield disposed within and co-extruded with said shaft in substantially spaced surrounding relationship and substantially coextensive with said electrical conductor, said shield being fabricated from a flexible metal wire braided cylinder.

2. The instrument of claim 1 in which said electrically insulative material forming said shaft exhibits a relative dielectric constant of less than about seven to said applied current.

3. The instrument of claim 1 in which said electrically insulative material forming said shaft is substantially hydrophobic.

4. The instrument of claim 1 in which:

said elongate shaft is cylindrical, is symmetrically disposed about said axis, and has a first diameter at said surface as said first principal cross-sectional dimension;

said electrical conductor is cylindrical, is symmetrically disposed about said axis, and has a second diameter as said second principal cross-sectional dimension; and the ratio of said first diameter to said second diameter is at least about 2.

5. The instrument of claim 1 wherein said shaft is formed from at least one of the following: polymeric material, glass, and ceramic material.

6. The instrument of claim 5 wherein said polymeric material is one or more of the following: polyether ether ketone, polyether sulfone, polyarylether ketone, polyamide, polytetrafluoroethylene, polyethylene, polypropylene, and polycarbonate.

7. The instrument of claim 6 in which said shaft is formed by extrusion, injection molding or casting.

8. The instrument of claim 6 wherein said polymeric material is reinforced with one or more of glass fiber, glass microspheres, ceramic fiber, and ceramic microspheres.

9. The instrument of claim 1 in which said source is located remotely from said instrument and includes said return ground, and said shield is connectable with said return ground.

10. The instrument of claim 1 including an internally disposed central conduit extending along said shaft in spaced adjacency with said electrical conductor which is selectively fluid communicable with suction and irrigation sources.

11. The instrument of claim 1 wherein:

said elongate shaft is configured having an elongate first cavity formed therein;

including a stationary insert formed of a polymeric electrically insulative material, having an outwardly disposed surface supporting a metallic, electrically conductive shield and located within said first cavity; and said electrical conductor is located within said stationary insert.

12. The instrument of claim 11 in which said shaft and said stationary insert are formed from at least one of the following: polyether ether ketone, polyether sulfone, polycrystalether ketone, polyamide, or polytetrafluorethylene, homogenous (unfilled) polymeric material, glass (fiber)

filled polymeric material, hollow, electrically insulating microspheres dispersed in polymeric material, ceramic (fiber) filled polymeric material, polyamide, polyethylene, polypropylene, and polycarbonate.

13. The instrument of claim 1 wherein the radius of the conductive member is between about 0.2 mm to about 0.4 mm and the radius of the elongate shaft is between about 2.5 mm and about 9 mm.

14. An monopolar electrosurgical instrument for carrying out surgical procedures upon tissue within a body in contact with a return ground by insertion through access openings of minimal size, comprising:

an elongate shaft of length along a central axis suited for accessing said tissue, having a working end, a grasping end, an external surface of a configuration exhibiting a first principal cross-sectional dimension permitting a slidable insertion thereof through said opening into said body, said shaft being formed of an electrically insulative material and having a first elongate cavity disposed therein of second principal cross-sectional dimension;

an electrically conductive working tip assembly secured to said working end, reciprocally actuable to surgically engage said tissue and responsive to an applied current at predetermined frequency for surgical application thereof to select portions of said tissue;

a hand engageable handle coupled with said shaft at said grasping end and having a movable component with a drive portion generally reciprocally movable in correspondence with movement of said movable component;

a generally cylindrical elongate driveshaft formed of an electrically insulating material, having an outwardly disposed surface extending about a longitudinal axis at a third principal cross-sectional dimension, slidably positioned within said first elongate cavity and extending between a forward end connected in reciprocal drive relationship relative to said working tip and a rearward portion connected in reciprocally driven relationship with said handle movable component drive portion;

an electrical terminal supported at said handle, having an input connectable with a source of said current and an output; and an electrical conductor supported concentrically within said driveshaft, extending therealong in current transfer communication between said electrical terminal output and said electrically conductive working tip.

15. The instrument of claim 14 in which said electrical conductor has a fourth principal cross-sectional dimension selected as effective to convey said applied current to said electrically conductive working tip and to lower capacitive coupling between said conductor and said tissue adjacent said shaft external surface to an extent substantially atraumatic to said adjacent tissue.

16. The instrument of claim 15 including:

a shaft connector mounted upon said handle movable component at said drive portion, configured for receiving and retaining said driveshaft rearward portion and through which said electrical conductor extends; and said electrical terminal is supported upon said handle movable component, is movable therewith and is connected with said electrical conductor as it extends through said shaft connectors.

17. The instrument of claim 14 wherein said shaft and driveshaft are formed from at least one of the following: polymeric material, glass, and ceramic material.

18. The instrument of claim 17 wherein said polymeric material is at least one of the following: polyether ether ketone, polyether sulfone, polycrystalether ketone, polyamide, or polytetrafluoroethylene, polyethylene, polypropylene, and polycarbonate.

19. The instrument of claim 18 wherein said polymeric material is reinforced with at least one of the following: glass fiber, glass microspheres, ceramic fiber, and ceramic microspheres.

20. The instrument of claim 16 in which:

said shaft connector receives and retains said driveshaft for imparting said reciprocal motion thereto while permitting the rotation thereof about said longitudinal axis; and said electrical terminal is coupled to and rotatable with said driveshaft about said longitudinal axis.

21. The instrument of claim 14 in which said driveshaft outwardly disposed surface supports a metallic, electrically conductive shield.

22. The instrument of claim 14 in which:

said elongate shaft is cylindrical, is symmetrically disposed about said central axis, and has a first diameter at said surface as said first principal dimension;

said electrical conductor is cylindrical, is symmetrically disposed about said central axis and has a second diameter; and the ratio of said first diameter to said second diameter is at least about 2.

23. The instrument of claim 14 wherein the radius of the conductive member is between about 0.2 mm to about 0.4 mm and the radius of the elongate shaft is between about 2.5 mm and about 9 mm.

24. An instrument for carrying out monopolar electrosurgical procedures upon tissue within a body in contact with a return ground by insertion of said instrument through minimal size openings to access said tissue, comprising:

an elongate shaft of length along a central axis suited for accessing said tissue, having a working end, a grasping end, an external surface of a configuration exhibiting a first principal cross-sectional dimension permitting a slidable insertion thereof through said opening into said body, said shaft being formed of an electrically insulative material and having an elongate cavity disposed therein of second principal cross-sectional dimension;

an electrically conductive working tip assembly supported at said working end, reciprocally actuable to surgically engage said tissue and responsive to an applied current at predetermined frequency for surgical application thereof to select portions of said tissue;

a hand engageable handle coupled with said shaft at said grasping end and having a movable component with a drive portion generally reciprocally movable in correspondence with movement of said movable component;

an elongate draftshaft formed of electrically conductive material, having an outwardly disposed surface extending about a longitudinal axis at a third principal cross-sectional dimension, slidably positioned within said elongate cavity and extending between a forward end connected in current transfer and reciprocal drive relationship with said working tip and a rearward portion connected in reciprocally driven relationship with said handle movable component drive portion;

an electrically conductive shield located within said shaft outwardly of said cavity and inwardly of said shaft outwardly disposed external surface, in spaced surrounding relationship and substantially coextensive with said cavity Said shield being fabricated from a flexible metal wire braided cylinder;

an electrical terminal assembly supported at said handle, having a first input connectable with a source of said current said source being remotely located form said instrument and deriving said return ground, a second input connectable with said return ground, having a first output connecting said drive shaft in current transfer relationship with said first input, and a second output connecting said second input with said shield.

25. The instrument of claim 24 in which said shield is a flexible metal wire cylinder coextruded with said shaft.

26. The instrument of claim 24 in which said first and second inputs of said electrical terminal assembly are connectively incompatible to an extent effective to prevent coupling said second input with said source of current.

27. The instrument of claim 24 in which said electrical terminal assembly first output includes a first brush in slidable engagement with said drive shaft and said second output includes a second brush in slidable engagement with said shield.

28. The instrument of claim 24 wherein the radius of the conductive member is between about 0.2 mm to about 0.4 mm and the radius of the elongate shaft is between about 2.5 mm and about 9 mm.

29. An instrument for carrying out monopolar electrosurgical procedures upon tissue within a body in contact with a return ground by insertion of said instrument through minimal size openings to access said tissue, comprising:

an elongate shaft of length along a given axis suited for accessing said tissue, having a working end, a grasping end and an exterior surface of configuration exhibiting a first principal cross-sectional dimension permitting the slidable insertion thereof through said opening into said body, said shaft being formed of an electrically insulative material and having a first elongate cavity disposed therein;

an electrically conductive working tip assembly supported at said working end responsive to an applied current at predetermined frequency for surgical application thereof to select portions of said tissue;

an electrical terminal supported at said shaft grasping end, having an input connectable with a source of said current and an output;

an electrical conductor supported within said shaft, extending therealong in current transfer communication between said electrical terminal output and said working tip and having a second principal cross-sectional dimension substantially less than said first principal cross sectional dimension selected as effective to convey said applied current to said working tip and to lower capacitive coupling between said conductor and said tissue adjacent said exterior shaft surface to an extent substantially atraumatic to said adjacent tissue;

a stationary insert formed of a polymeric electrically insulative material, having an outwardly disposed surface supporting a metallic, electrically conductive shield and located within said first cavity; and said electrical conductor is located within said stationary insert.

30. The instrument of claim 29 wherein the radius of the conductive member is between about 0.2 mm to about 0.4 mm and the radius of the elongate shaft is between about 2.5 mm and about 9 mm.

31. An monopolar electrosurgical instrument for carrying out surgical procedures upon tissue within a body in contact with a return ground by insertion through access openings of minimal size, comprising:

an elongate shaft of length along a central axis suited for accessing said tissue, having a working end, a grasping end, an external surface of a configuration exhibiting a first principal cross-sectional dimension permitting a slidable insertion thereof through said opening into said body, said shaft being formed of an electrically insulative material and having a first elongate cavity disposed therein of second principal cross-sectional dimension;

an electrically conductive working tip assembly supported at said working end, reciprocally actuable to surgically engage said tissue and responsive to an applied current at predetermined frequency for surgical application thereof to select portions of said tissue;

a hand engageable handle coupled with said shaft at said grasping end and having a movable component with a drive portion generally reciprocally movable in correspondence with movement of said movable component;

an elongate driveshaft formed of an electrically insulating material, having an outwardly disposed surface extending about a longitudinal axis at a third principal cross-sectional dimension, slidably positioned within said first elongate cavity and extending between a forward end connected in reciprocal drive relationship with said working tip and a rearward portion connected in reciprocally driven relationship with said handle movable component drive portion;

an electrical terminal supported at said handle, having an input connectable with a source of said current and an output;

an electrical conductor supported within said driveshaft, extending therealong in current transfer communication between said electrical terminal output and said electrically conductive working tip, wherein said electrical conductor has a fourth principal cross-sectional dimension selected as effective to convey said applied current to said electrically conductive working tip and to lower capacitive coupling between said conductor and said tissue adjacent said shaft external surface to an extent substantially atraumatic to said adjacent tissue;

a shaft connector mounted upon said handle movable component at said drive portion, configured for receiving and retaining said driveshaft rearward portion and through which said electrical conductor extends; and said electrical terminal is supported upon said handle movable component, is movable therewith and is connected with said electrical conductor as it extends through said shaft connector.

32. The instrument of claim 31 wherein the radius of the conductive member is between about 0.2 mm to about 0.4 mm and the radius of the elongate shaft is between about 2.5 mm and about 9 mm.

* * * * *